US012611114B2

(12) United States Patent     (10) Patent No.:   US 12,611,114 B2

Faircloth     (45) Date of Patent:     Apr. 28, 2026

(54) BROADBAND MULTISPECTRAL DIAGNOSTIC SYSTEMS AND METHODS

(71) Applicant: Brian Faircloth, Evergreen, CO (US)

(72) Inventor: Brian Faircloth, Evergreen, CO (US)

( * ) Notice: Subject to any disclaimer, the term of this patent is extended or adjusted under 35 U.S.C. 154(b) by 1149 days.

(21) Appl. No.: 17/485,972

(22) Filed: Sep. 27, 2021

(65) Prior Publication Data

US 2022/0095937 A1     Mar. 31, 2022

Related U.S. Application Data

(60) Provisional application No. 63/083,294, filed on Sep. 25, 2020.

(51) Int. Cl.

| | |
|---|---|
| *A61B 5/026* | (2006.01) |
| *A61B 5/0295* | (2006.01) |
| *A61B 5/1455* | (2006.01) |

(52) U.S. Cl.

CPC .......... *A61B 5/0261* (2013.01); *A61B 5/0295* (2013.01); *A61B 5/1455* (2013.01); *A61B 2562/0238* (2013.01)

(58) Field of Classification Search

CPC ... A61B 5/0261; A61B 5/0295; A61B 5/1455; A61B 2562/0238; A61B 5/0013; A61B 5/14551; A61B 5/6826; A61B 5/6852; A61B 5/7257; A61B 5/0075

See application file for complete search history.

(56) References Cited

U.S. PATENT DOCUMENTS

| | | | |
|---|---|---|---|
| 4,732,476 A | | 3/1988 | Barshad |
| 5,813,987 A | * | 9/1998 | Modell ................. A61B 5/0062 |
| | | | 600/476 |
| 6,438,399 B1 | | 8/2002 | Kurth |
| 6,711,426 B2 | | 3/2004 | Benaron et al. |
| 6,766,184 B2 | | 7/2004 | Utzinger et al. |
| 9,078,619 B2 | | 7/2015 | Panasyuk et al. |
| 10,772,541 B2 | | 9/2020 | Klein et al. |
| 2007/0015981 A1 | | 1/2007 | Benaron et al. |
| 2007/0263214 A1 | * | 11/2007 | Fateley .............. G02B 26/0841 |
| | | | 359/615 |
| 2009/0048502 A1 | | 2/2009 | Benaron et al. |
| 2014/0092288 A1 | | 4/2014 | Hattery et al. |
| 2017/0055894 A1 | | 3/2017 | Panasyuk et al. |
| 2020/0138360 A1 | * | 5/2020 | Fan ........................ A61B 5/441 |

FOREIGN PATENT DOCUMENTS

WO     91/01678     2/1991

OTHER PUBLICATIONS

Amini, M., 2016. A novel optical probe for detection of hypoxia in the deeper layers of human buccal tissue. Thesis for degree of Doctor of Philosophy (Ph.D.); Department of Mechanical, Electronics & Chemical Engineering, Faculty of Technology, Art & Design, Oslo & Akershus University College of Applied Sciences, Oslo, Norway. (pp. 1-106).

Bale, G., Mitra, S., Meek, J., Robertson, N. and Tachtsidis, I., 2014. A new broadband near-infrared spectroscopy system for in-vivo measurements of cerebral cytochrome-c-oxidase changes in neonatal brain injury. Biomedical optics express, 5(10). (17 pages).

Benaron, D.A. and Stevenson, D.K., 1994. Resolution of near infrared time-of-flight brain oxygenation imaging. Oxygen Transport to Tissue XV. (pp. 609-610).

Fathipour, V., Wheaton, S., Johnson, W.E. and Mohseni, H., Sep. 2016, Modeling of a sensitive time-of-flight flash LiDAR system. In Infrared Sensors, Devices, and Applications VI (vol. 9974, p. 99740N). International Society for Optics and Photonics. doi: 10.1117/12.2236506. (pp. 99740N-1 to 99740N-10).

Torres Filho, I.P., Temer, J., Pittman, R.N., Proffitt, E. and Ward, K.R., 2008. Measurement of hemoglobin oxygen saturation using Raman microspectroscopy and 532-nm excitation. Journal of applied physiology, 104(6), pp. 1809-1817. Downloaded from journals. physiology, org/journal.jappl (174.198.132.179) on Sep. 16, 2020. (pp. 1809-1817).

Giannoni, L., Lange, F. and Tachtsidis, I., 2018. Hyperspectral imaging solutions for brain tissue metabolic and hemodynamic monitoring: past, current and future developments. Journal of Optics, 20(4). (pp. 1-25).

Halicek, M., Fabelo, H., Ortega, S., Callico, G.M. and Fei, B., 2019. In-vivo and ex-vivo tissue analysis through hyperspectral imaging techniques: revealing the invisible features of cancer. Cancers, 11(6). (pp. 1-30).

Huang, J. (2012). Multispectral Imaging of Skin Oxygenation [Doctoral dissertation, Ohio State University]. OhioLINK Electronic Theses and Dissertations Center. http:/rave.ohiolink.edu/etdc/view?acc_num=osu1356637098. (pp. i to xviii; pp. 1-203).

(Continued)

*Primary Examiner* — Abid A Mustansir

(74) *Attorney, Agent, or Firm* — Acuity IP, LLC; Nathan S. Cassell

(57) ABSTRACT

Exemplary diagnostic systems and methods involve delivering multispectral light to a tissue of a patient, detecting light from the tissue, and analyzing the tissue based on the detected light. Light delivery can be achieved using a multi-dispersion element monochromator apparatus that includes a broad spectrum light source, a rotating body, and multiple dispersion elements in operative association with the rotating body.

19 Claims, 28 Drawing Sheets

(56)              References Cited

OTHER PUBLICATIONS

Huang, J., Zhang, S., Gnyawali, S., Sen, C.K. and Xu, R.X., 2015. Second derivative multispectral algorithm for quantitative assessment of cutaneous tissue oxygenation. Journal of biomedical optics, 20(3). (pp. 036001-1 to 036001-12).

Jacques, S.L., 2013. Optical properties of biological tissues: a review. Physics in Medicine & Biology, 58(11). (pp. R37-R61).

Kulcke, A., Feiner, J., Menn, I., Holmer, A., Hayoz, J. and Bickler, P., 2016. The Accuracy of Pulse Spectroscopy for Detecting Hypoxemia and Coexisting Methemoglobin or Carboxyhemoglobin. Anesthesia & Analgesia, www. anesthesia-analgesia.org. (pp. 1-10).

Kymissis, I.J. and Pervez, N., Full spectral pulse oximetry using the Chromation system. www.chromation.com. (pp. 2/1 to 2/2).

LeBoeuf, S.F., Zhang, H. and Muth, J.F., 2012, August. Custom visible to infrared, multi-wavelength light emitters for pulse oximeter applications. In 2012 Annual International Conference of the IEEE Engineering in Medicine and Biology Society. IEEE. (pp. 1184-1187).

Lu, G. and Fei, B., 2014. Medical hyperspectral imaging: a review. Journal of biomedical optics, 19(1). (pp. 010901-1 to 010901-23).

Lund University. Atomic Physics. Photon Time-of-Flight Spectroscopy (pToFS). https//www.atomic.physics.lu.se/research/biophotonics/facilities-and-equipment/photon-time-of-flight-spectroscopy-ptofs/. Sep. 16, 2020 (1 page).

MacKenzie, L.E. and Harvey, A.R., 2018. Oximetry using multispectral imaging: theory and application. Journal of Optics. Downloaded from https://www.researchgate.net/publication/323810046. DOI: 10.1088/2040-8986/aab74c. (pp. 1-43).

Maniewski, Roman & Liebert, Adam & Kacprzak, Michal & Zbieae, A. (2004). Selected applications of near infrared optical methods in medical diagnosis. Opto-Electronics Review. 12, No. 3. (pp. 255-262).

Morimoto, A., Nakamura, S., Sugino, M., Koyano, K., Htun, Y., Arioka, M., Fuke, N., Mizuo, A., Yokota, T., Kato, I. and Konishi, Y., 2019. Measurement of the Absolute Value of Cerebral Blood Volume and Optical Properties in Term Neonates Immediately after Birth Using Near-Infrared Time-Resolved Spectroscopy: A Preliminary Observation Study. Applied Sciences, 9(10). Doi:3390/App9102172. www.mdpi.com/journal/applsci. (pp. 1 of 9-9 of 9).

Meyers, D.E., Anderson, L.D., Seifert, R.P., Ortner, J.P., Cooper, C., Beilman, G.J. and Mowlem, J.D., 2005. Noninvasive method for measuring local hemoglobin oxygen saturation in tissue using wide gap second derivative hear-infrared spectroscopy. Journal of biomedical optics, 10(3). Downloaded from https://www.spiedigitallibrary.org/journals/Journal of-Biomedical-Optics on Sep. 16, 2020. (pp. 034017-1 to 034017-18).

Ohmae, E., Oda, M., Suzuki, T., Yamashita, Y., Kakihana, Y., Matsunaga, A., Kanmura, Y. and Tamura, M., 2007. Clinical evaluation of time-resolved spectroscopy by measuring cerebral hemodynamics during cardiopulmonary bypass surgery. Journal of biomedical optics, 12(6). (pp. 062112-1 to 062112-9).

Saso, S., Clancy, N.T., Jones, B.P., Bracewell-Milnes, T., Al-Memar, M., Cannon, E.M., Ahluwalia, S., Yazbek, J., Thum, M.Y., Bourne, T. and Elson, D.S., 2018. Use of biomedical photonics in gynecological surgery: a uterine transplantation model. Future science OA, 4(4). (18 pages).

Sowa, M.G., Sep. 2019, SnapshotNIR: a handheld multispectral imaging system for tissue viability assessment. In Photonics and Education in Measurement Science 2019 (vol. 11144). International Society for Optics and Photonics. doi: 10.1117/12.2534989. (pp. 111440B-1 to 111440B-6).

Takatani, S., Cheung, P.W. and Ernst, E.A., 1980. A noninvasive tissue reflectance oximeter. Annals of biomedical engineering, 8(1). (1 page).

Tsiakaka, O., Gosselin, B. and Feruglio, S., 2020. Source-Detector Spectral Pairing-Related Inaccuracies in Pulse Oximetry: Evaluation of the Wavelength Shift. Sensors, 20(11). (pp. 1 of 17-17 of 17).

Von Chong, A., Terosiet, M., Histace, A. and Romain, O., 2019. Towards a novel single-LED pulse oximeter based on a multispectral sensor for IoT applications. Microelectronics Journal, 88. www.elsevier.com/locate/mejo. https://doi.org/10.1016/j.mejo.2018.03.005. (pp. 128-136).

PCT International Search Report; Int'l Application No. PCT/US2021/052171; Issued Dec. 23, 2021; (3 pages).

* cited by examiner

Path difference = d (sinθ₁,sinθₘ)

Liquid Light Guide Transmission

Fused Silica Fiber Transmission

Effective Attenuation Coefficient (Breast Tissue)

Efficiency versus wavelegth

NIR Single Photon Detector

Human Head Berth

| Sex | Percentile (centimetres) | | | | |
|---|---|---|---|---|---|
| | 1st | 5st | 50th | 95th | 99th |
| Man | 13.9 | 14.3 | 15.2 | 16.1 | 16.5 |
| Women | 13.3 | 13.7 | 14.4 | 15.0 | 15.8 |

1000

1002

1004 — Processor(s)

1010 — Storage device(s)

1006 — Input device(s)

1008 — Output device(s)

1012 — Communications Subsystem

Working memory — 1004

Operating system — 1016

Application(s) — 1018

BROADBAND MULTISPECTRAL DIAGNOSTIC SYSTEMS AND METHODS

CROSS-REFERENCE

This application claims the benefit of U.S. Provisional Patent Application No. 63/083,294 filed Sep. 25, 2020, the content of which is incorporated herein by reference.

BACKGROUND

Embodiments of the present invention related generally to systems and methods for analyzing tissue, proteins, amino acids, chemicals, and other substances or molecules in the human body.

Various diagnostic devices and methods have been proposed for analyzing body tissues and other biological parameters of a patient, such as oxygen or hemoglobin in the blood.

Although currently available diagnostic modalities can provide physicians and other medical professionals with valuable information concerning the health of a patient, still further improvements are desired. Embodiments of the present invention address at least some of these outstanding needs.

SUMMARY

Embodiments of the present invention encompass systems and methods for scanning across a broad spectrum from UV to near infrared (NIR) to short wave infrared (SWIR), and outputting a very narrow wavelength selection (e.g. by using a monochromator). In some cases, a fast scan monochromator can be used, particularly in instances where a high scan rate is desirable (e.g. intra heart pulse diagnostics). Delivery device embodiments disclosed herein can be used to deliver the spectral light to its point of use. A number of interchangeable detectors that vary the functionality and capabilities of the apparatus can be used, including for example, photodiodes, CCD arrays, spectrometers, optical spectrum analyzers, photomultipliers or single photon detectors/counters, and the like. Certain Fourier transform infrared spectroscopy techniques are described to allow Fourier transform spectroscopy in the UV-NIR spectral range. In some cases, a light pulse time of flight 3D imaging system can be used to differentiate tissue types during the imaging process either through index of refraction, scatter, and absorption changes throughout the volume or by time of flight spectroscopy to identify particular atom/molecule species through their excitation and re-emission times. Embodiments also encompass sub-configurations that returns spectral data (i.e. Raman scatter shifts and fluorescence) on the tissue being imaged. Embodiments of the present invention encompass 3D imaging systems that produce an internal image of a substantial volume of the body, and that also identify atomic, molecular, or chemical species contained within that volume, as well as de facto individual tissue types, such as healthy or diseased tissue within that volume. In some cases, one or more of the apparatus elements can have wavelength dependent efficiencies. In some cases, in order to get calibrated results, it can be helpful to factor out these inefficiencies, and/or to calibrate the apparatus (e.g. at time of manufacture) to account for those efficiencies. In some cases, a single diagnostic type can be performed. In some cases, any number of the diagnostic technologies disclosed herein can be used simultaneously or in conjunction to improve the overall diagnostic accuracy and functionality.

Embodiments of the present invention encompass broadband multispectral systems and methods for analyzing a tissue of a patient. Exemplary broadband multispectral systems can include a light source providing an output of light across a broad spectral range, a dispersion element, a first aperture mechanism disposed between the light source and the dispersion element, a delivery system. a second aperture mechanism disposed between the dispersion element and the delivery system, and a detector mechanism. In some cases, the first aperture mechanism allows a portion of the light output by the light source to pass therethrough. In some cases, the dispersion element spatially separates the portion of the light into components of different wavelengths. In some cases, the second aperture mechanism allows an amount of the light separated by the dispersion element to pass therethrough. In some cases, the delivery system transmits the amount of light toward the tissue of the patient to produce resulting light. In some cases, the detector mechanism detects the resulting light. According to some embodiments, the broad spectral range encompasses electromagnetic radiation across a wavelength band from 100 nm to 2000 nm. In some instances, the dispersion element includes a rotating body having a grating element. In some instances, the dispersion element includes a rotating body having multiple grating elements, and the entirety of the broad spectral range is scanned multiple times throughout one rotation of the rotating body. In some instances, the dispersion element includes a ring having grating lines etched around a circumference thereof. In some instances, the dispersion element includes a cylinder having grating lines etched around a circumference thereof. In some instances, the light source includes a Xenon arc lamp, a halogen lamp, a carbon arc lamp, a light emitting diode, a laser diode, any combination of one or more thereof. In some instances, the dispersion element one or more grating devices and/or one or more prism devices. In some instances, the detector mechanism includes a photodiode, a CCD array, a spectrometer, an optical spectrum analyzer, a photomultiplier, a single photon detector, a single photon counter, or any combination of one or more thereof. In some instances, the delivery system includes a fiber, a fiber bundle, a liquid light guide, a gel light guide, or any combination of one or more thereof.

In another aspect, embodiments of the present invention encompass methods of gathering data from a patient. For example, a method of gathering diagnostic data throughout a heartbeat of a patient can include providing an output of light across a broad spectral range, spatially separating the output using a dispersion element, sequentially transmitting selected wavelengths of the separated output through a delivery system toward a skin surface of a patient to produce resulting light, and detecting the resulting light with a detector mechanism. Parameters of the resulting light can change throughout the heartbeat. In some cases, the parameters correspond to changing blood volume throughout the heartbeat. In some cases, the parameters correspond to changing blood concentration throughout the heartbeat.

In still another aspect, embodiments of the present invention can include a multi-dispersion element monochromator apparatus for use in a broadband spectral diagnostic system. An exemplary monochromator apparatus can include a light source providing an output of light across a broad spectral range, a rotating body (for example a ring or a cylinder), and multiple dispersion elements in operative association with the rotating body. In some cases, one rotation of the rotating body enables multiple narrow bandwidth scans across the entirety of the broad spectral range. In some cases, rotation of the rotating body enables scanning on the order of 10,000's nm/sec and dozens of spectral scans per second. In some cases, at least one of the multiple dispersion elements comprises a grating device. In some cases, at least one of the multiple dispersion elements provides a full spectrum scan twice per rotation. In some cases, the light source includes a Xenon arc lamp, a halogen lamp, a carbon arc lamp, a light emitting diode, a laser diode, or any combination thereof. In some cases, the broad spectral range encompasses electromagnetic radiation across a wavelength band from 100 nm to 2000 nm.

In yet another aspect, embodiments of the present invention encompass systems and methods for analyzing one or more tissues of a patient. Exemplary methods can include delivering multispectral light to the one or more tissues of the patient, detecting light from the one or more tissues, and analyzing the one or more tissues based on the detected light.

In another aspect, system and method embodiments for analyzing a tissue of a patient can include delivering multispectral light to the tissue of the patient, detecting light from the tissue, and analyzing the tissue based on the detected light.

BRIEF DESCRIPTION OF THE DRAWINGS

The novel features of the invention are set forth with particularity in the appended claims. A better understanding of the features and advantages of the provided system and methods will be obtained by reference to the following detailed description that sets forth illustrative embodiments, in which the principles of the invention are utilized, and the accompanying drawings of which:

DETAILED DESCRIPTION

Figures 1A, 1B:
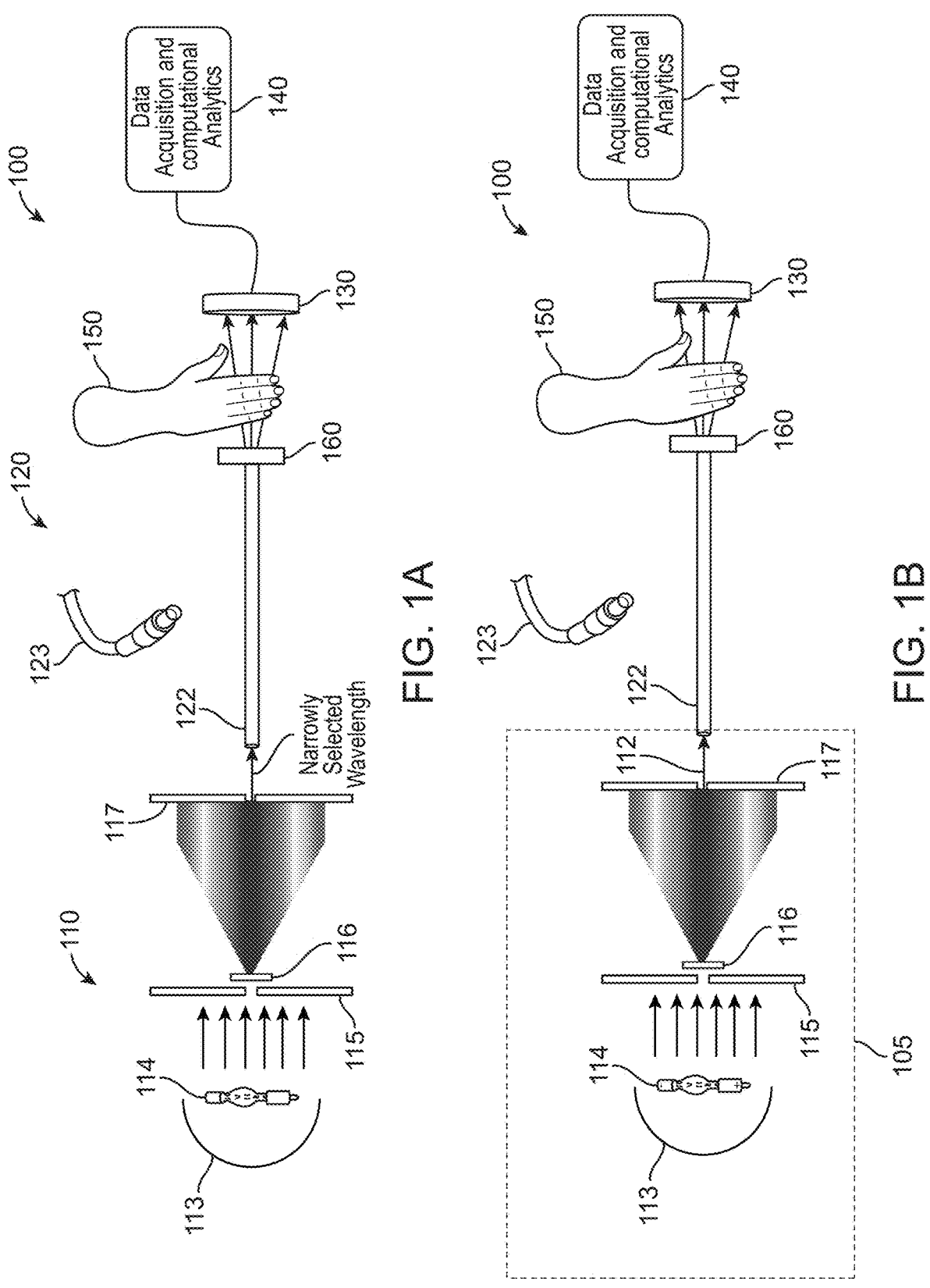
FIGS. 1A and 1B depict aspects of a multispectral diagnostic system, according to embodiments of the present invention.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In some embodiments, systems and methods provide attenuation, scatter, and differential spectroscopy scans across a very broad spectral range from ultra-violet (UV) to short wave infrared (SWIR). In some embodiments, the forward and backward scatter profiles can be mapped across the proposed spectral range. Since tissue, blood, and their constituents scatter coefficients vary as a function of wavelength, diagnostic information can be gained by analyzing these scatter profiles as a function of wavelength. In some embodiments, Raman scattering can be used across the proposed broad spectral range to identify compounds and/or molecules of target specimens in the blood and tissue. In some embodiments, Fourier transform infrared spectroscopy techniques can be used that allow for Fourier transform spectroscopy in the UV-NIR wavelength range. In some embodiments, time of flight imaging techniques can be used to image and identify tissue inside the body using light pulses. Data obtained by such system and method embodiments can involve the interaction and detection of multiple conditions, states, and measurement of various quantities, and machine learning, artificial intelligence, and data analytics can be used to process such data.

In some cases, the spectral range is from about 100 nm to about 2000 nm. In some cases, in vivo imaging and diagnostic techniques can involve tissue penetration depths that are greater than 4 mm. In some cases, in vivo imaging and diagnostic techniques can involve tissue penetration depths that are sufficiently great to identify a brain tumor. In some cases, in vivo imaging and diagnostic techniques can involve tissue penetration depths that are sufficiently great to identify other anatomical features. In some cases, in vivo imaging and diagnostic techniques can involve analyzing oxygen and/or hemoglobin amounts or concentrations. Some embodiments can involve using narrow wavelengths with a mechanisms such as a monochromator combined with Raman scattering or fluorescence to identify and/or analyze other useful substance/molecules, such as enzymes, amino acids, drugs, chemicals, and the like. In some embodiments, time of flight measurements can be used for internal imaging of the body, and when combined with Raman Spectroscopy can identify the imaged object in the body and its constituents. Such techniques can help to detect and map tumors, damaged tissue, hemorrhagic events, or any other number of medical objects or events.

FIGS. 1A and 1B depict aspects of broadband multispectral diagnostic systems, according to embodiments of the present invention. As shown here, a broadband multispectral diagnostic systems system 100 can include a broad-spectrum light source 110, a delivery system 120, and a detector 130. The detector 130 can be in operative connectivity with a computer system or device 140 configured to perform data acquisition and computational analytics. In some embodiments, the computer system or device 140 can include one or more features of a computer system or device configured to perform methods disclosed herein, such as computer system or device 1000 depicted in FIG. 27. The broad-spectrum light source 110 can operate to select a very narrow wavelength band 112 or particular wavelength in the spectrum and can include a monochromator 105. In some embodiments, a Fourier transform spectroscopy method can be incorporated, which uses the full wavelength range at once. The target 150 (e.g. tissue) can be placed directly at the output of the monochromator 105. In some cases, the light can be delivered through a delivery system 120 which can include a fiber (e.g. such as delivery fiber 122), fiber bundle, or liquid or gel light guide (e.g. such as a light guide 123). In some cases, light guide 123 can be a liquid light guide (420-2000 nm). Optics 160 may additionally be added to collimate the output beam if desired. The detector 130 and/or computer system or device 140 can operate to determine much of the functionality and diagnostic data that may be collected and analyzed. The present application discloses several embodiments that determine different diagnostic capabilities. The system 100 can be configured such that the type of detector used can be interchangeable.

As shown here, the light source 110 can include a reflector 113, a light or source of photons 114, a first aperture mechanism 115, a grating or gratings 116, and a second aperture mechanism 117. In operation, a monochromator 105 can be used to select and transmit a narrow band of wavelengths of light or other radiation, for example selected from a wider range of wavelengths provided by the light or source of photons 114. Although FIGS. 1A and 1B depict operation of the system 100 to analyze the tissue of the patient by sending light through the skin surface, it is understood that techniques disclosed herein can be used when sending light through internal surfaces or tissues within the patient. For example, one or more components of the delivery system 120 can be placed, advanced, and/or retracted within a scope or catheter that is at least partially positioned within the patient. In such embodiments, aspects of the system 100 can be maneuvered to various desired locations within the patient's body, such as the vasculature or other lumens, cavities, or passages. For example, the catheter or other guiding instrument can be placed in the patient's body, and one or more components of the system 100 can delivered or placed via the catheter or guiding instrument to analyze vascular tissue, cardiovascular tissue, urological tissue, gastrointestinal tissue, neurovascular tissue, ophthalmic tissue, or any other desired or target tissue of a patient. According to some embodiments, the light source or the sensor can be positioned inside the body or a body cavity via a scope or catheter and the sensor or light source respectively can be outside the body or in another body cavity.

Figure 2A:
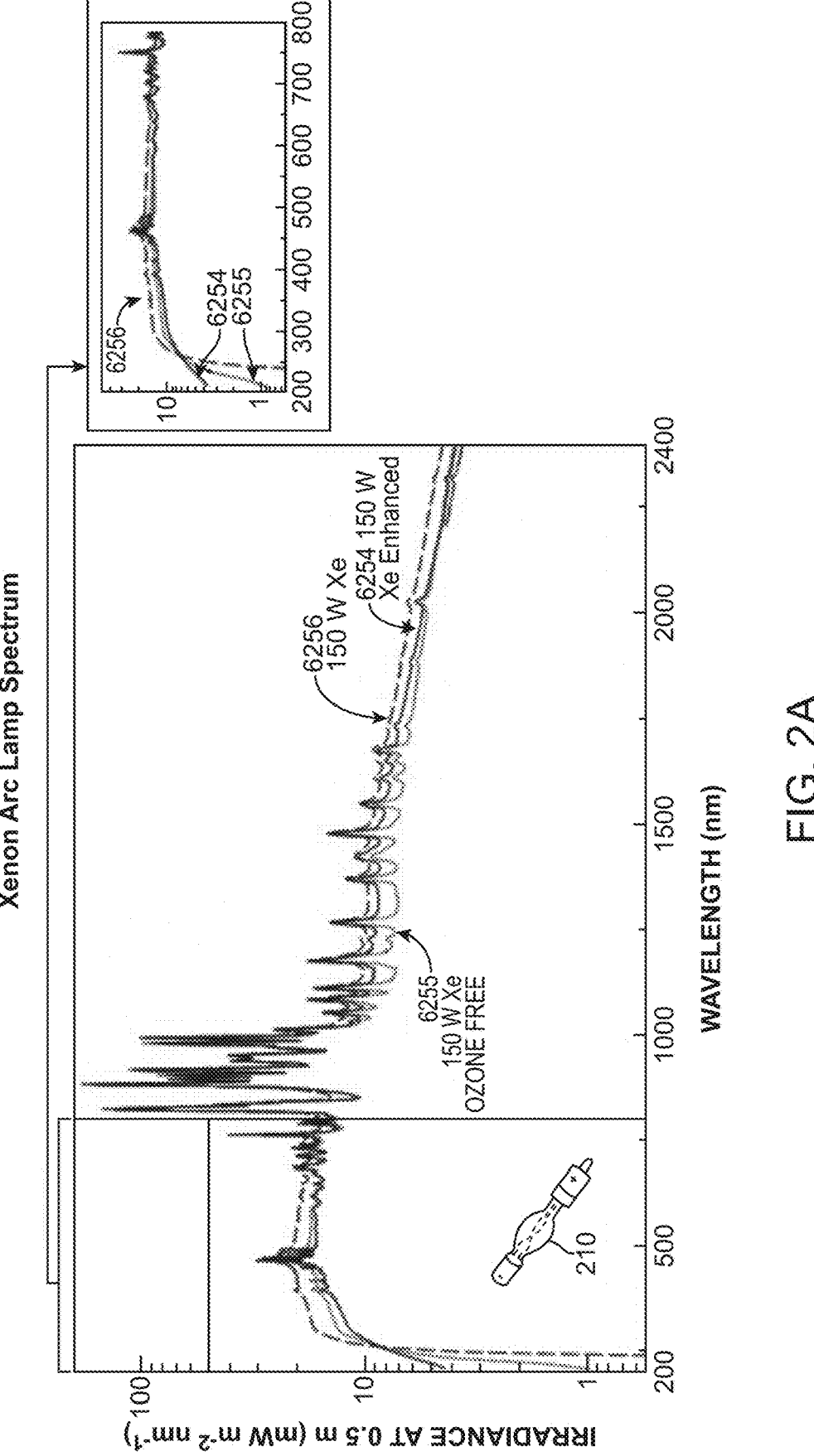
FIGS. 2A and 2B depict aspects of a multispectral diagnostic system gratings, according to embodiments of the present invention.
Figure 2B:
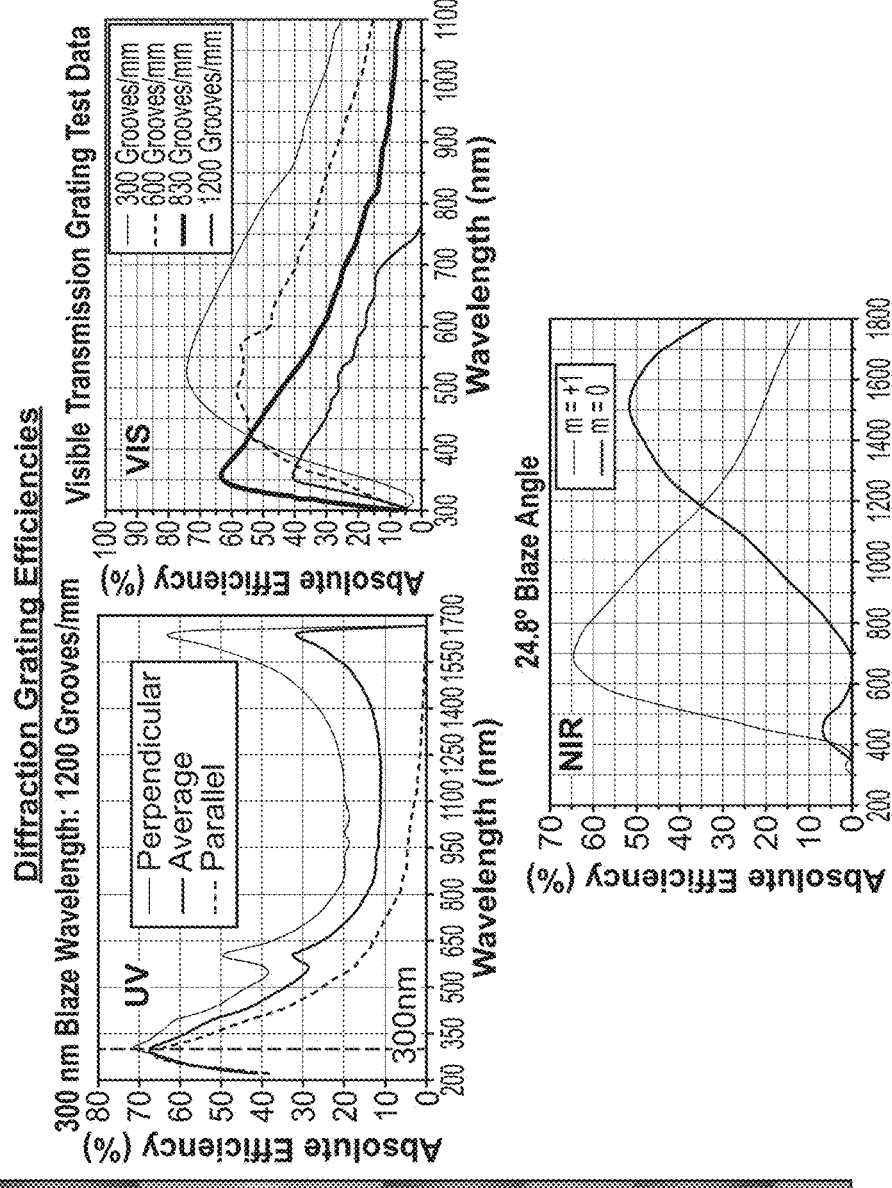
Figure 5:
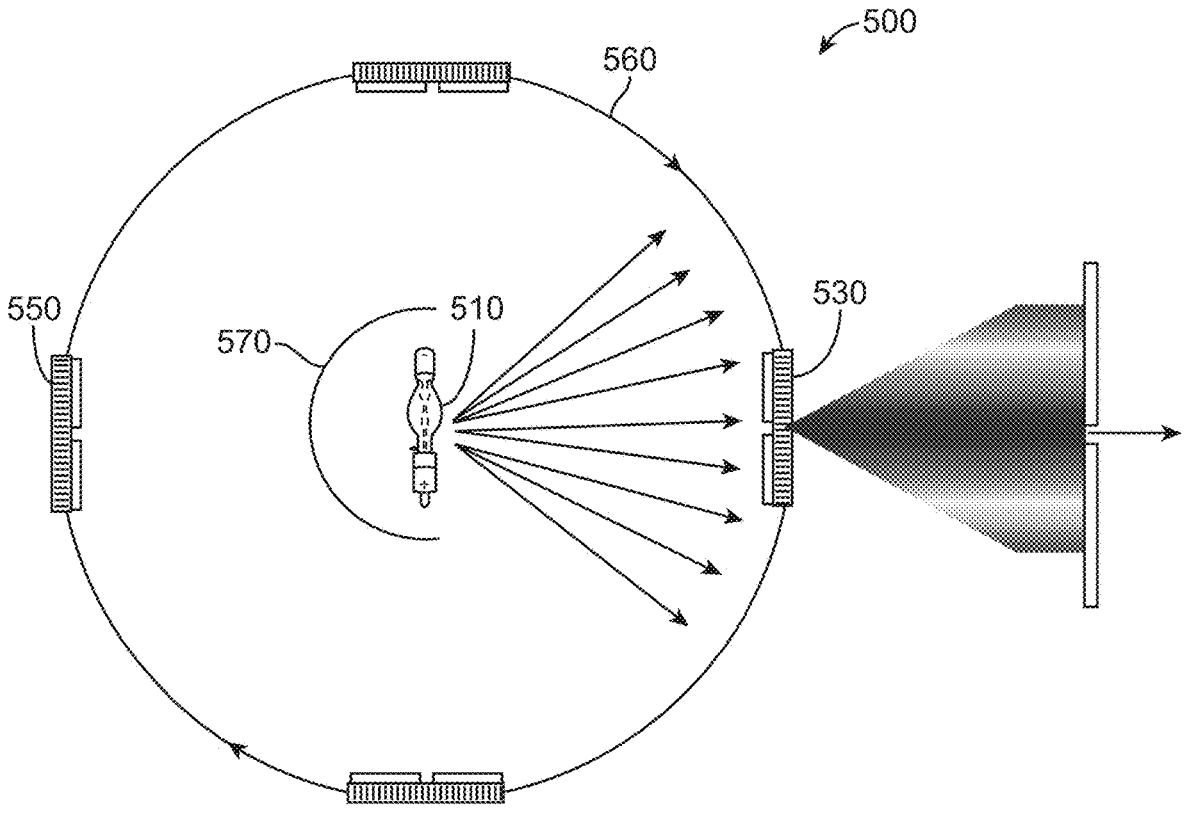
FIG. 5 depicts aspects of a multispectral diagnostic system monochromator, according to embodiments of the present invention.

FIGS. 2A and 2B depict aspects of light or spectral sources 210, according to embodiments of the present invention. In some cases, a source of photons 210 that generates power in a broad spectral range can be used. Exemplary light sources include Xenon arc lamps, which produce very broad spectral output at high power levels. In other embodiments, light sources can include halogen lamps, carbon arc lamps, LEDs, laser diodes, and the like. Gratings 220 or prisms 230 can be used to spatially separate the spectrum. In some cases, a diffraction grating can be used. In some cases, gratings can be used because of their linearity. Due to the broad spectrum desired to be sampled, which may be UV to shortwave infrared (SWIR) [e.g. 100 nm-2000 nm], a compound grating may be used. That is, a grating 220 that incorporates the characteristics of multiple gratings that are wavelength sensitive into a single grating. The grating can change characteristics along its length. In some instances, the lines per millimeter of the grating can change along its length. In some cases, grating element 220 can incorporate the elements of different wavelength gratings into a single element, for example by incorporating multiple gratings (each covering a wavelength range) into a single grating. This can be done by adjusting the lines per millimeter along the length of the grating so that one part of the grating may operate in the UV and Visible and another part of the same grating, further down the grating, may work in the near infrared, thus allowing a single grating element to cover a wide wavelength range. It is noted that the FIG. 5 depicts a monochromator having multiple gratings. Individual gratings of such a monochromator can include features similar those described here with regard to grating 220. The charts shown in FIG. 2B depict exemplary grating efficiencies as a function of wavelength. In some embodiments, SWIR may be referred to as far NIR.

Figure 3A:
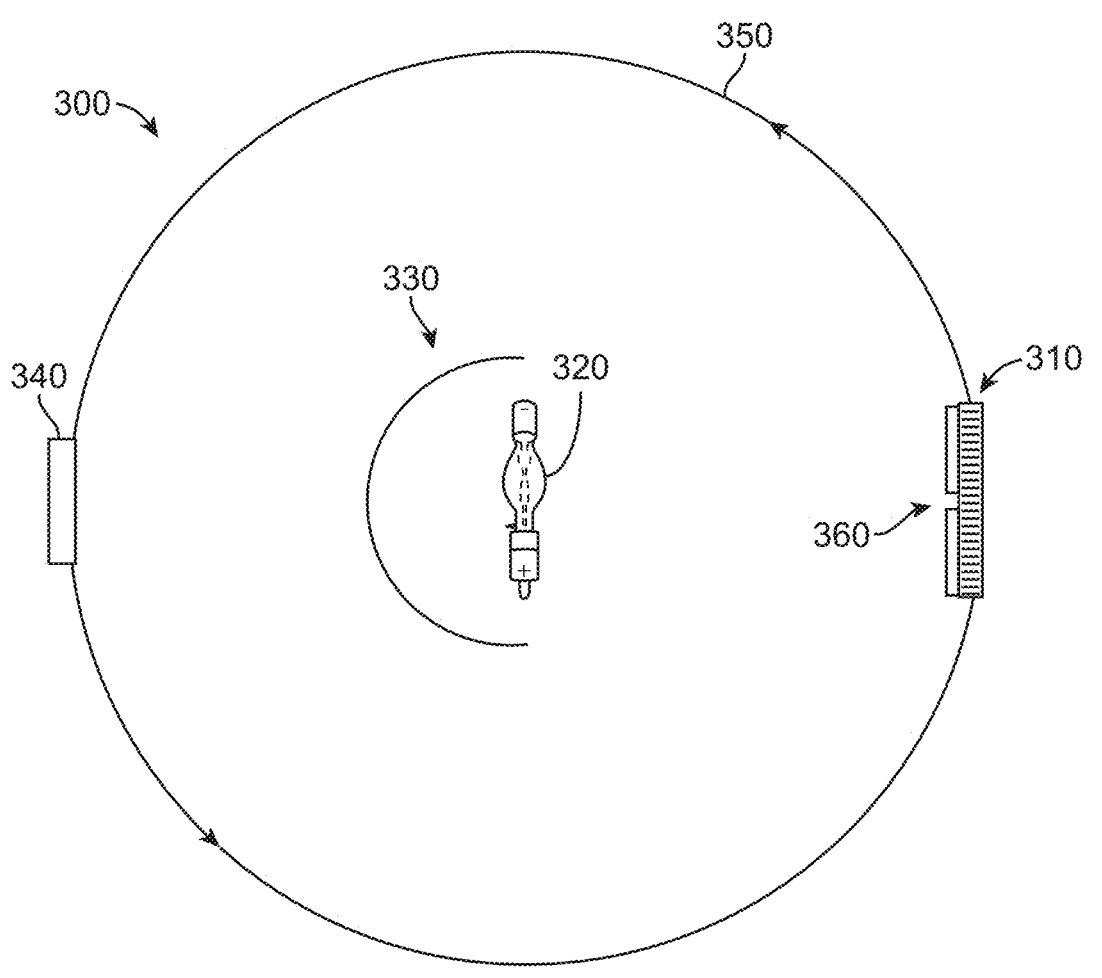
FIGS. 3A and 3B depict aspects of a multispectral diagnostic system monochromators, according to embodiments of the present invention.

FIG. 3 depicts aspects of a fast scan monochromator 300, according to embodiments of the present invention. Operation of the monochromator 300 can involve spinning the grating 310 on a counter balanced rigid body rotator 350 centered on the light source or source of photons 320, the light source or source of photons 320 being stationary. A balancing weight 340 can provide a counter balance (e.g. a counter balance to the weight of the grating 310). Light can be reflected using a reflector 330. For example, the reflector 330 can reflect and concentrate light from the source of photons 320 toward the grating 310. At a modest 2400 rotations per minute (40 rotations per second), if an individual scan covered 700 nm (300 nm to 1000 nm for instance) this would be a scan rate of 56,000 nm/sec (including the positive and negative diffraction orders). This can be for a single grating. In other embodiments, multiple gratings can be spaced around the circumference of the rotating body to increase the scan rate by several times as described elsewhere herein. The grating aperture or aperture slit 360 can be stationary or integrated into the grating 310. Any number of methods can be used to incorporate the aperture slit on the grating including without limitation silkscreen, photo-lithography, and ink jet. The aperture 360 can operate to limit the solid angle the grating sees from the light source or source of photons 320. Because the dispersion is a function of incident angle, enhanced wavelength sensitivity can be achieved with a light source that is further away and an aperture that is smaller A balancing weight 340 can be used to keep the center of mass at the center of rotation, and thus the angular momentum vector stationary. Otherwise the angular momentum vector may process and cause instabilities of the mechanical system.

A grating equation (Equation 1) can apply for both reflective and transmissive gratings.

$$\Theta_m = \arcsin\left(\sin\theta_i - \frac{m\lambda}{d}\right) \quad \text{(Equation 1)}$$

Figure 3B:
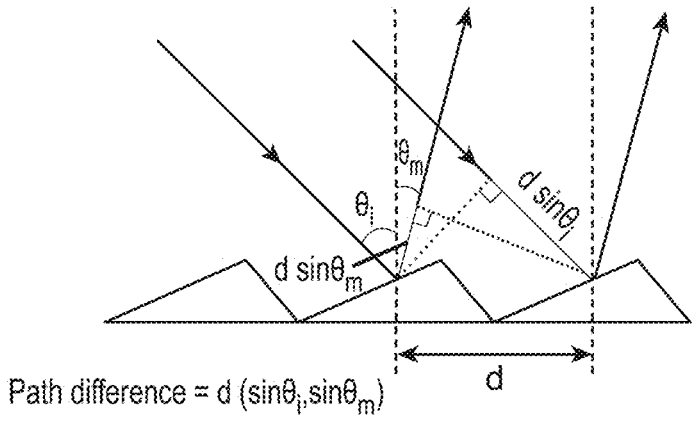

In this equation, $\theta_m$ is the diffracted angle, $\theta_i$ is the incident angle, m is the diffraction order number, $\lambda$ is the wavelength of light, and d is the spacing between grating elements. The angle at which light exits the grating is dependent on the wavelength of light (the dispersive element of the grating) as well as the incident angle of the light. When a broad band light source is used the output spectrum can be steered by adjusting the incident angle, for example with mechanical actuators or gimbles to adjust the angle of the grating relative to the light source. Additional aspects of the equation parameters are depicted in FIG. 3B.

The high scan rates achieved by fast scan monochromators disclosed herein are well suited for use in gathering diagnostic data throughout a heartbeat, as the blood volume and concentration parameters can change throughout the heartbeat. The spectrum can be scanned dozens of times per second to provide adequate time resolution for intra heartbeat diagnostics. In some embodiments, the presently disclosed monochromators can scan significantly higher than current commercially available monochromators which scan up to 500 nm/s. In some embodiments, the presently disclosed monochromators can scan on the order of 10,000's nm/sec and dozens of spectral scans per second, and such performance can be effective to obtain high resolution intra-heart pulse data across a broad spectrum. As an example, four grating elements can provide 8 full spectral scans per rotation. As another example, a dispersed grating spectrum covering ~2000 nm (100 to 2100 nm) can provide 16,000 nm/rotation. As another example, a rotational speed of 5 rotations per second can provide 80,000 nm/sec (e.g. 8 scans/rotation×2000 nm/scan×5 rotations/sec=80,000 nm/scan). In another example, a two grating system can provide 40,000 nm/sec. Hence, embodiments disclosed herein are well suited for use in intra heartbeat spectral diagnostics.

Figure 4A:
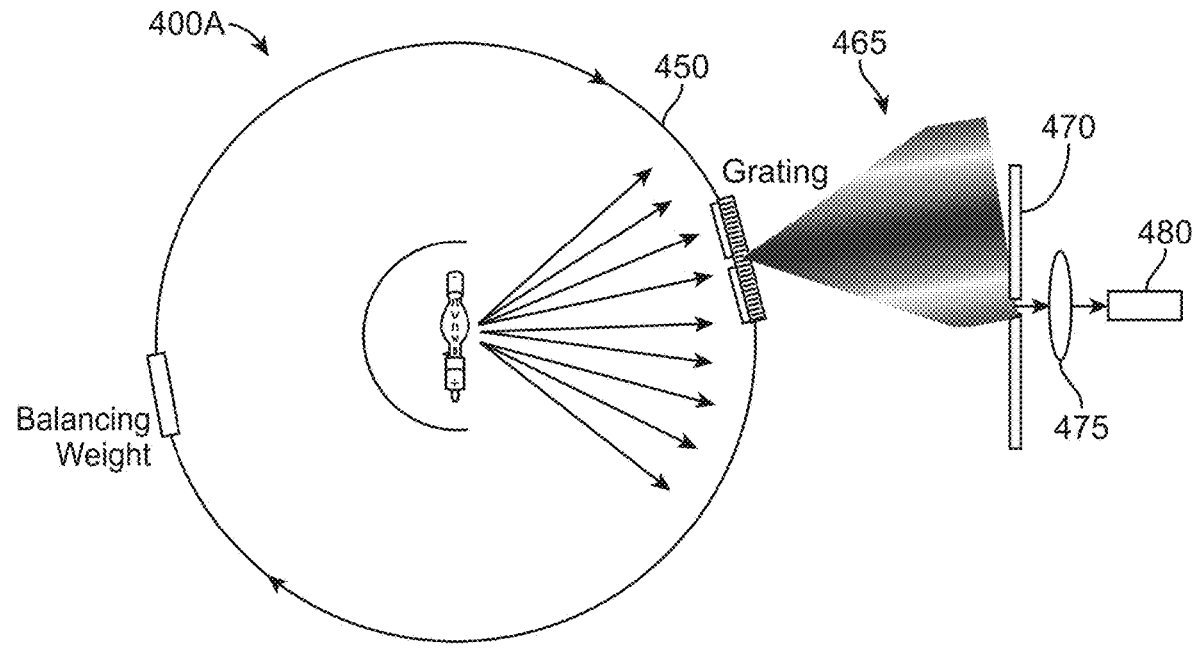
FIGS. 4A and 4B depict aspects of a multispectral diagnostic system monochromators, according to embodiments of the present invention.
Figure 4B:
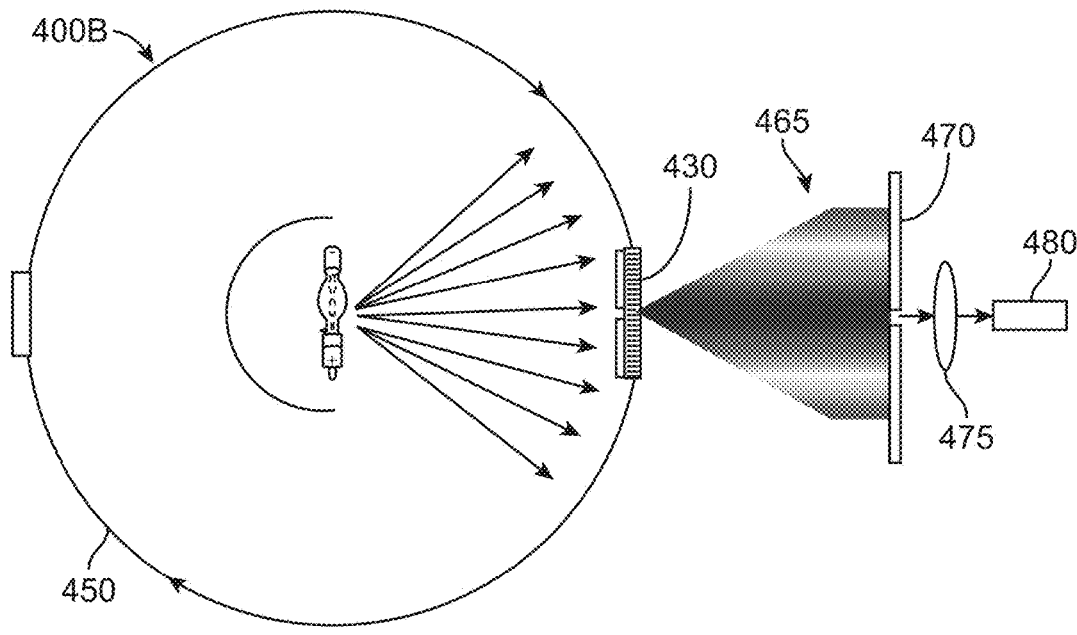

FIGS. 4A and 4B depict aspects of fast scan monochromator embodiments (400A, 400B), according to embodiments of the present invention. A beam can translate across the output slit by using a rigid body rotational method to spin the grating 430 on a rotating body 450. As shown here, an aperture or aperture mechanism 470 can be used to select a portion of the diffracted light 465, thereby allowing the portion of light to pass therethrough. A fiber optic, fiber bundle, or liquid or gel light guide could butt-couple to the output slit or the beam could be focused with optics 475 (e.g. one or more lens elements) into the fiber/light guide 480.

As shown in in the monochromator 500 embodiment depicted in FIG. 5, a counter balance can be replaced with another grating 550. Additional gratings can be added to increase the scan rate. As an example, if the body 560 is rotating at 2400 rpm, with a single grating 40 scans of the spectrum can be achieved per second. With four gratings, 160 spectrum scans per second can be achieved. In some cases, a single grating can create the spectrum twice—a mirror image of the spectrum around the centerline. For example, two gratings can scan the spectrum four times per rotation and four grating can scan the full spectrum eight times per rotation. In some cases, a spectrum scan can include a broadband spectrum scan (e.g. from UV to short-wave infrared (SWIR)). In other embodiments, more gratings can be used if desired. In some cases, the packing geometry of the gratings and output beam may limit the number of gratings. The reflector 570 can help concentrate the light energy from the photon source 510 onto the active, output, grating 530. In some embodiments, additional collimating and focusing optics (like those used in reflective telescopes) can be used to further concentrate the beam into an intense collimated beam, further increasing the output signal. Reflective optics can be used since reflective (e.g. mirrors) do not experience chromatic aberrations (aberrations due to spectral differences in the light). Embodiments of the present invention encompass the use of a multielement grating to cover from UV to SWIR in a single monochromator. In some embodiments, a glass ring or cylinder can be used in which the grating lines are etched around the circumference of the ring or cylinder. The grating pattern can be repeated periodically around the circumference as desired. Such embodiments can provide an excellent packing density of the gratings and would not require a counterbalance as well as provide continuous scanning without interruptions in the spectral output. It is understood that although transmission gratings are described, reflective gratings may also be used by repositioning the slit and output to correspond to a reflected spectrally dispersed beam as opposed to a forward transmitted spectrally dispersed beam. In some cases, a single light source or source of photons can provide the broadband spectrum, UV to short-wave infrared (SWIR) (e.g. 100 nm-2000 nm). In a non-limiting example, a Xenon arc lamp can be used as a single light source. In some cases, multiple light sources or sources of photons can be used, such as multiple LED's or multiple laser wavelengths both of which could be delivered via fiber optic(s) or waveguide(s) for instance. In some cases, the narrow output exiting the aperture or aperture mechanism can have a wavelength band width of <0.1 nm, or <1 nm, or <5 nm, or <10 nm depending on the grating design (e.g. lines per millimeter of the grating), the distance from the grating, and the width of the output aperture (aka slit). In some cases, a wavelength band having a greater width can provide light having a greater intensity. the more intense the light can be.

Figure 6:
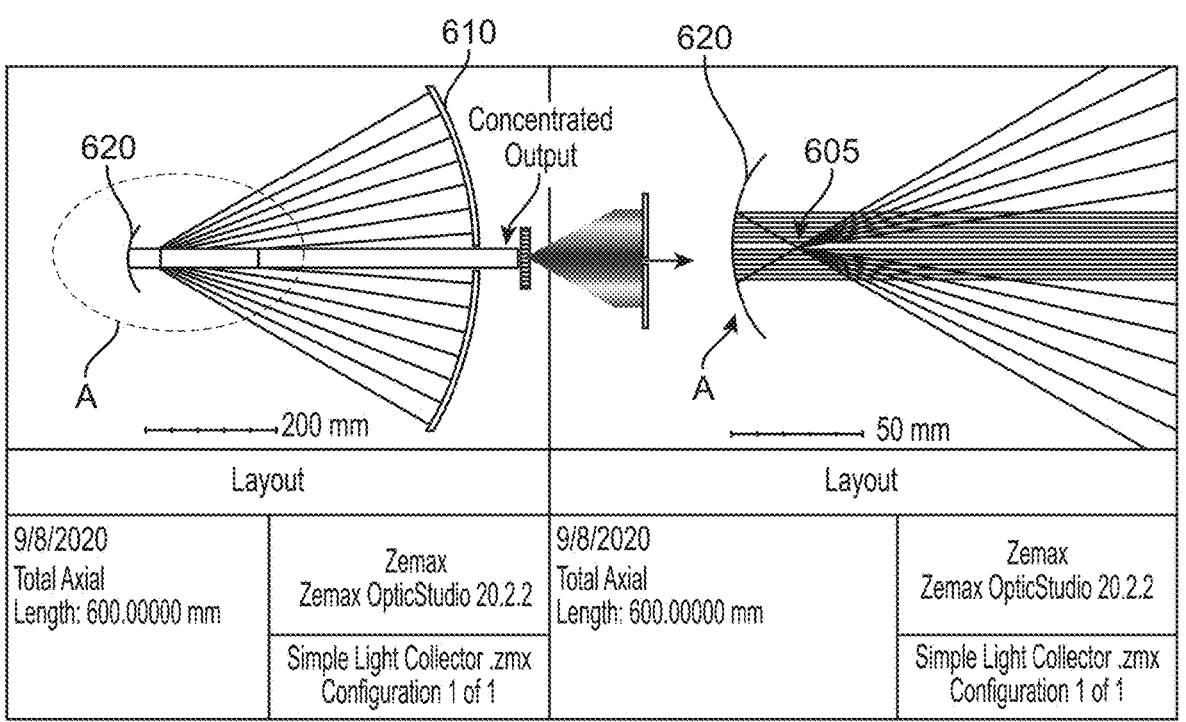
FIG. 6 depicts aspects of a multispectral diagnostic system monochromator, according to embodiments of the present invention.
Figure 6:
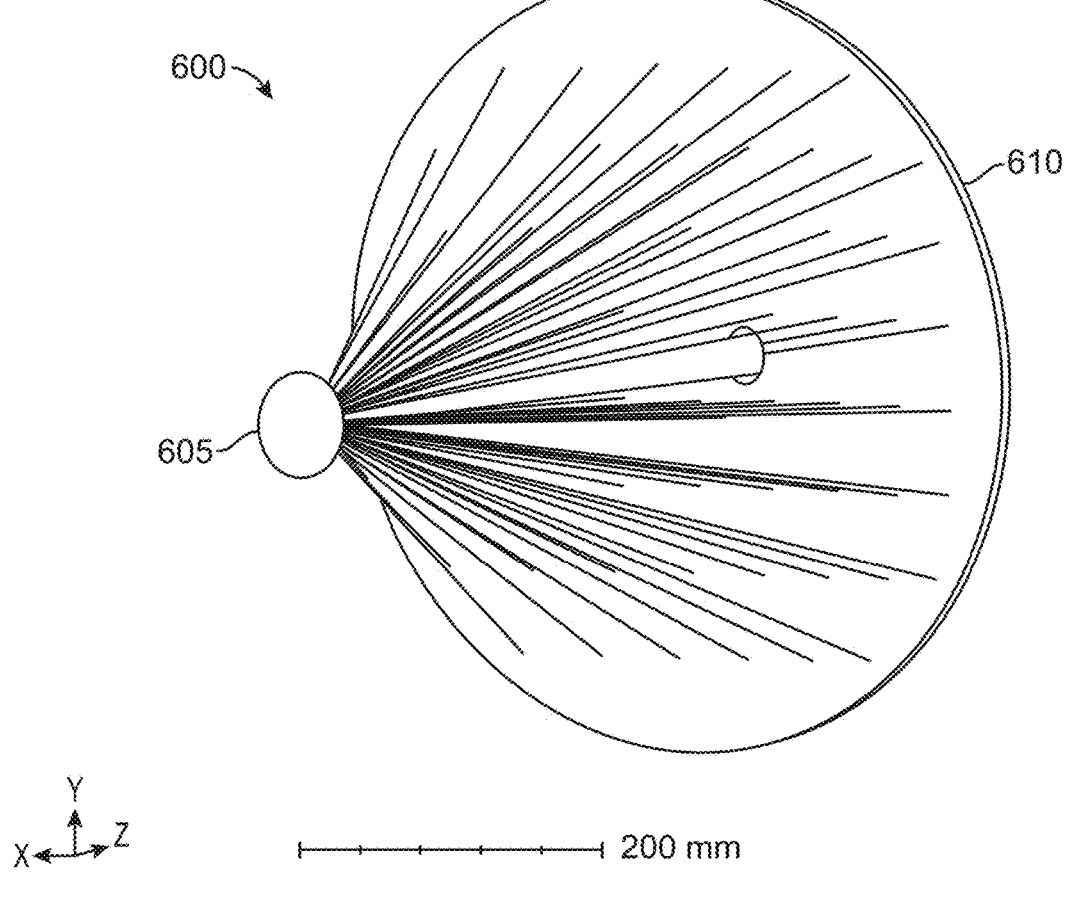

FIG. 6 depicts aspects of a monochromator light concentrator or optical system 600, according to embodiments of the present invention. Various optics can be used to further increase the intensity of the output beam. The optical system 600 shown here includes two parabolic mirrors or reflectors with their foci centered on the light source or source of photons 605. The larger mirror or reflector 610 captures light going to the right from the source 605 and retroreflects that light back through the source or very closely to the source. In some cases, direct overlap may cause overheating or damage to the source. The smaller mirror or reflector 620 captures and collimates the light from the source 605 heading to the left as well as collimating the retroreflected light from the larger mirror 610. Using these and similar embodiments, the intensity of the output can be increased several fold, depending on the size of the mirrors (including angular sweep) and the size of the source (e.g. smaller sources may be preferred, in some cases). In some cases, reflective optics may be preferred because mirrors do not experience chromatic dispersion.

As discussed elsewhere herein, the target (e.g. tissue) can be placed directly at the output of the monochromator. In some cases, a fiber optic, fiber bundle, or liquid or gel light guide can be used to deliver the light to a remote area such as an examination table or other point of use.

Figure 7:
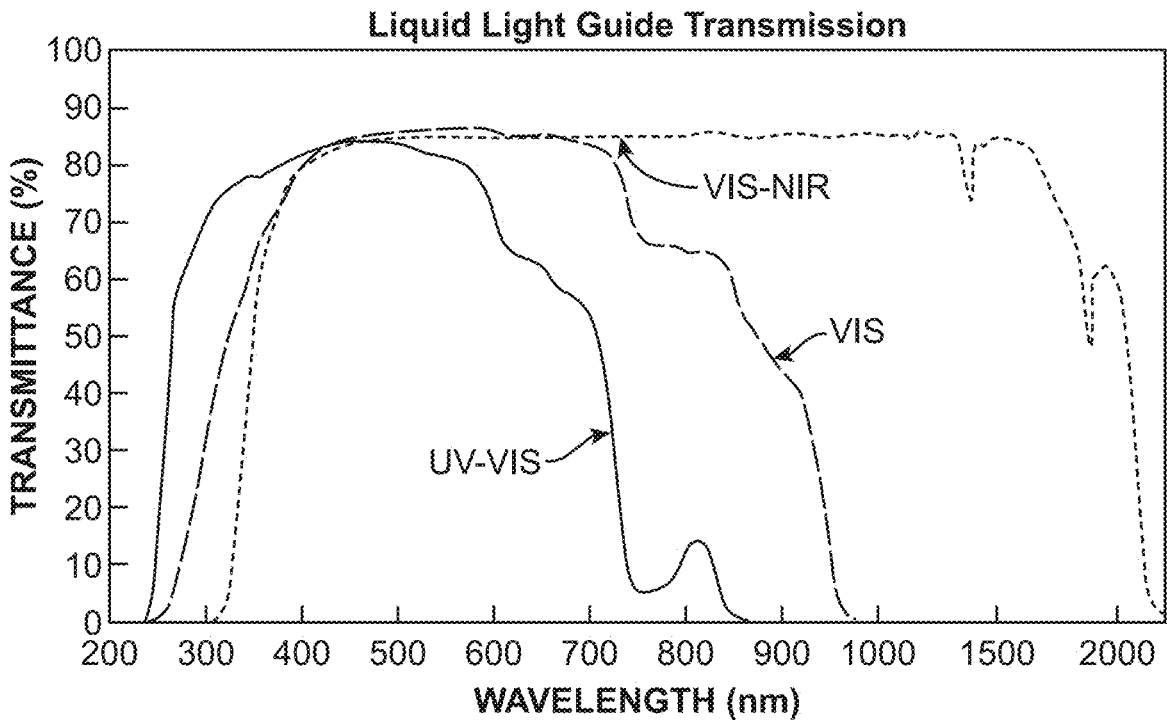
FIG. 7 depicts aspects of a multispectral diagnostic system light guide, according to embodiments of the present invention.
Figure 7:
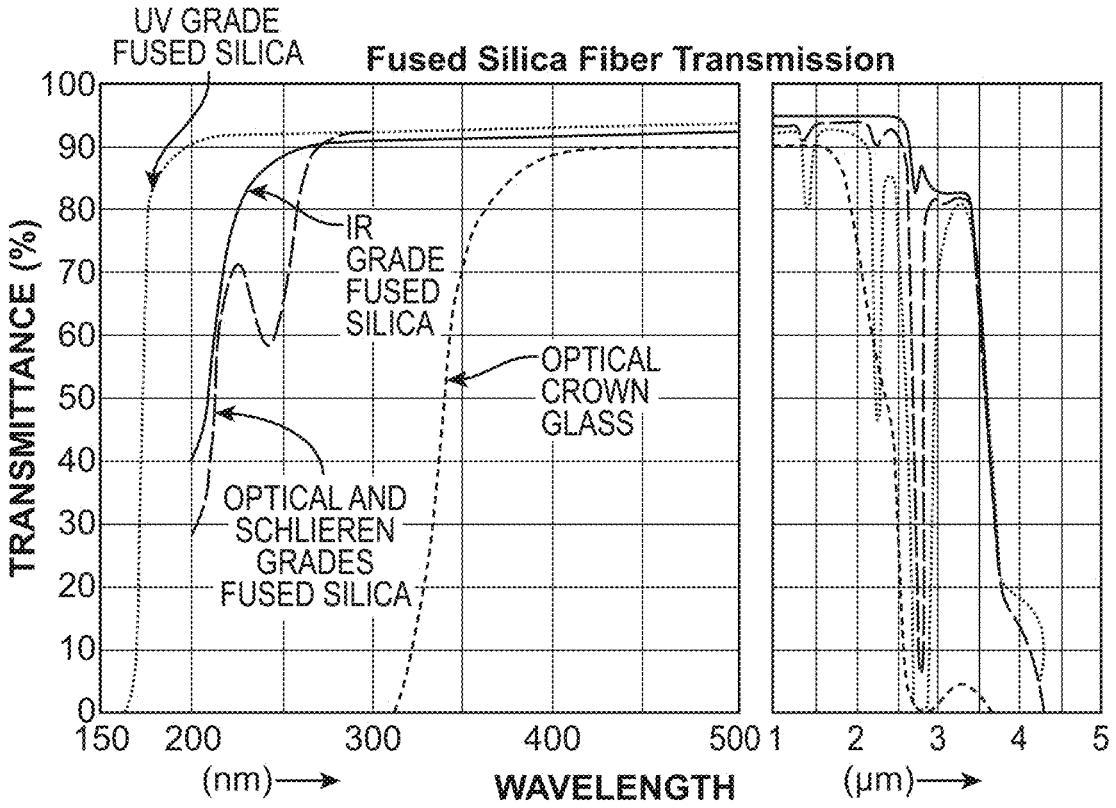

FIG. 7 depicts aspects of a delivery system, according to embodiments of the present invention. As discussed herein, the term "fiber" may refer to fiber optic, fiber bundle, or liquid or gel light guide. In some embodiments, liquid light guides that span the wavelengths of interest can be used. In some embodiments, fiber optics, such as fused silica, are capable of spanning the spectral range of interest. In some cases, which may involve the full spectral range from deep UV to NIR, two fibers can be used, where one is used for the UV and one is used for the remainder or another portion of the spectrum (as can be seen in the images shown in FIG. 7).

Figures 8A, 8B:
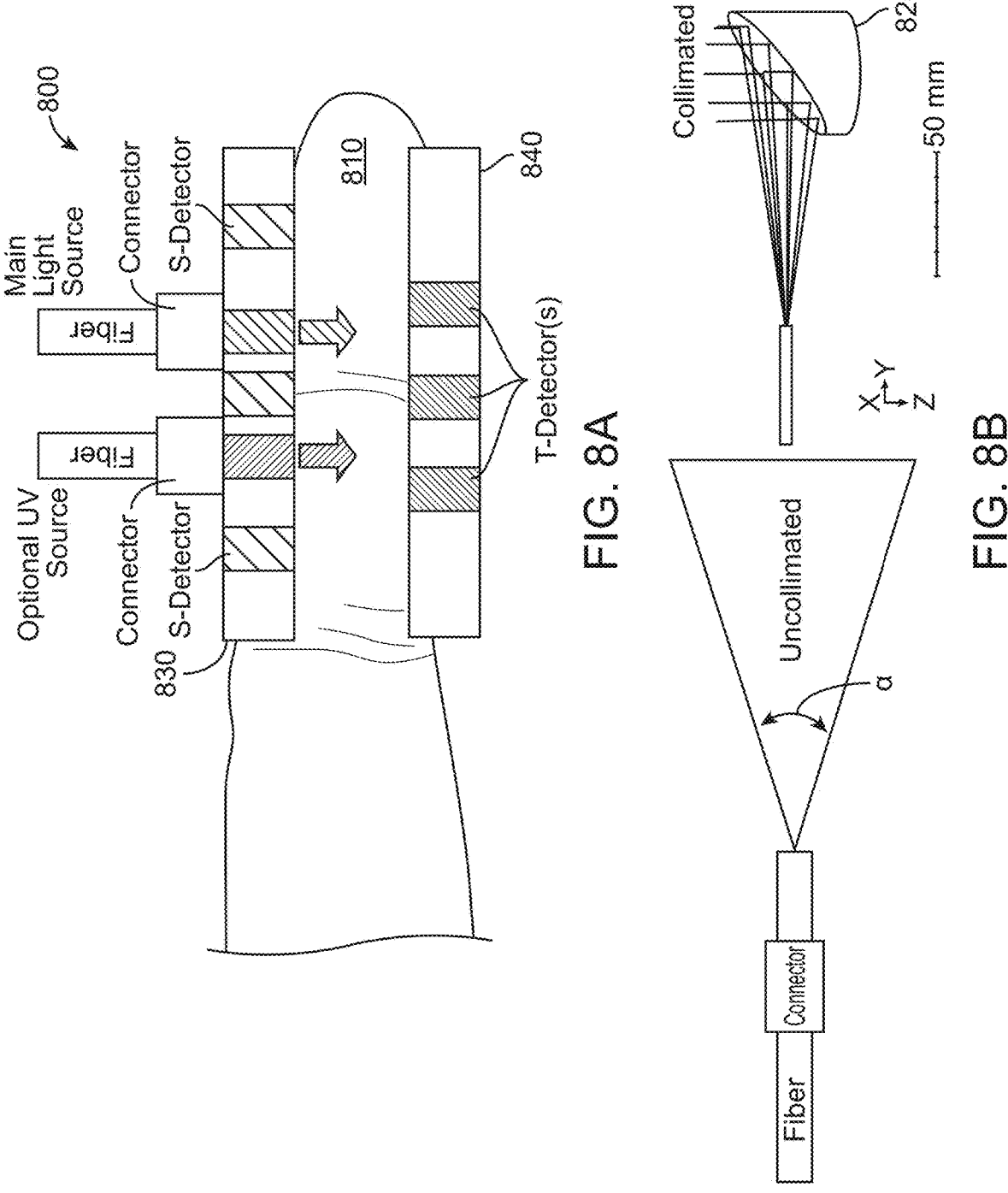
FIGS. 8A and 8B depict aspects of a multispectral diagnostic system, according to embodiments of the present invention.

FIGS. 8A and 8B depicts aspects of delivery systems, according to embodiments of the present invention. In some cases, the fiber can be terminated at a clamp-like device 800. In some cases, light can be provided to fiber by a main light source. In some cases, light can be provided to fiber by a UV source. The clamp 800 can affix the light delivery and detection device(s) to the preferred body part 810, such as a finger, toe, palm, ear lobe, fold of skin, or the like. Such clamping/affixing can be achieved through any of a variety of means. The T-Detectors are the transmission detectors, and they detect the light that passes through the body part. As shown here, T-Detectors can be positioned on a first device component 840. The S-Detectors are the scattered light detectors, and they detect the light that is back-reflected from the body part, which may be referred to as the target. As shown here, S-Detectors can be positioned on a second device component 830. The target tissue can be positioned between the first device component 840 and the second device component 830.

In some embodiments, as shown in FIG. 8B, light can exit a fiber/beam guide in a cone angle α. This angle can be very large depending on a number of factors, including without limitation the launch cone angle of the light into the proximal end of the fiber, tip, tilt, focus of the beam on the proximal fiber face, bending/flexing of the fiber, and length of the fiber. The light from the fiber(s) can be optically collimated so that the angular scatter profile of the light can be decoupled from the natural divergence of the beam exiting the fiber. This can allow for the light entering the target to be low angle, thus light scattered at higher angles after transmission can be identified as being scattered within the target exclusively.

In some cases, broadband refractive optics 820 can be used to collimate the beam from the fiber. In some cases, off axis-reflective (mirror) optics can also be used which would not incur chromatic aberrations or dispersion unlike refractive optics. In some cases, optics 820 can be provided as an off axis parabola collimator. Embodiments of the present invention encompass techniques for collimating a beam from a fiber, and in some cases this involves accommodating very broad spectral beams and using mirrors.

Figure 9:
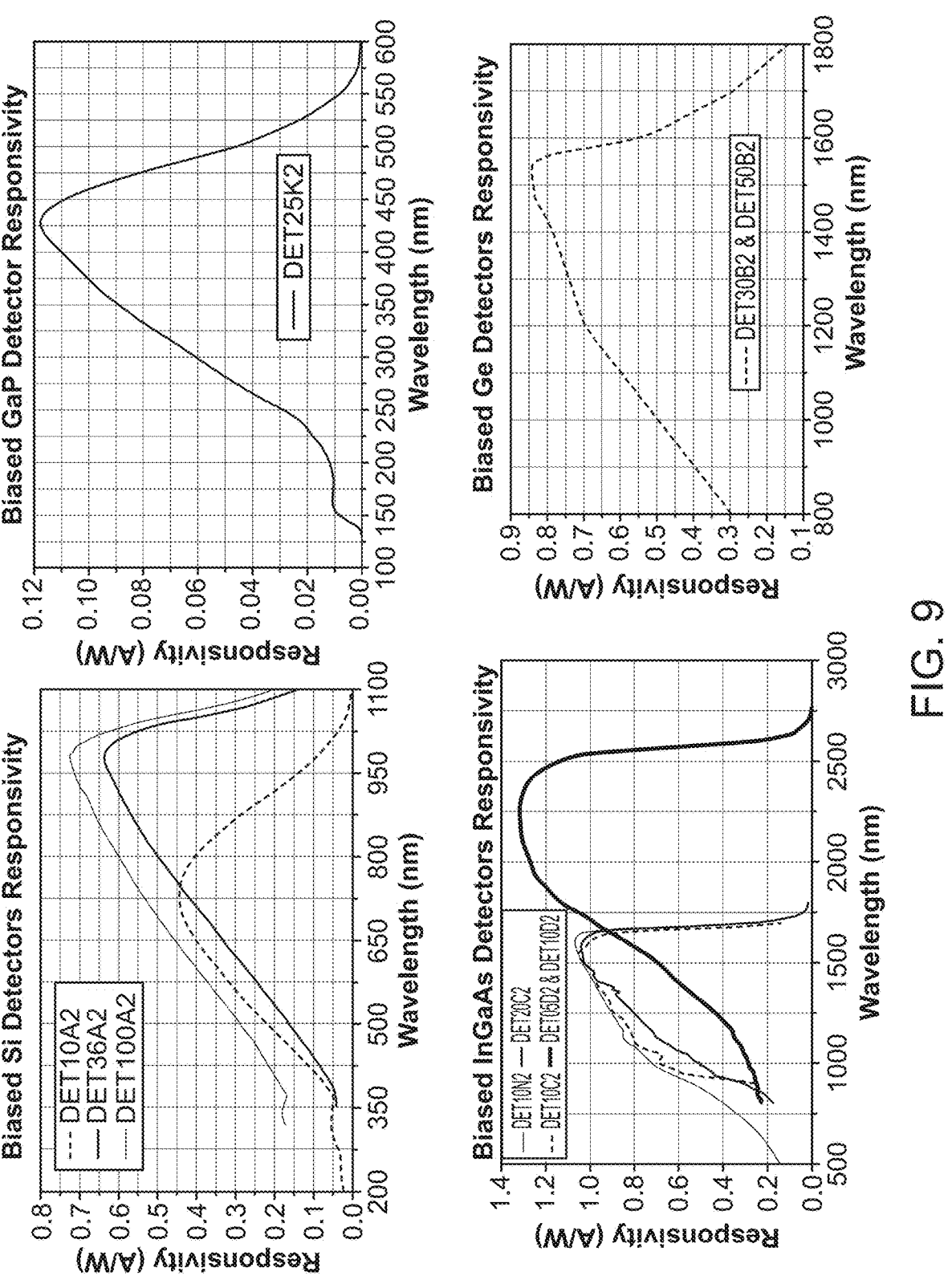
FIG. 9 depicts aspects of a multispectral diagnostic system detector, according to embodiments of the present invention.

As discussed elsewhere herein, a number of interchangeable detectors that vary the functionality and capabilities of the apparatus can be used, including for example, photodiodes, CCD arrays, spectrometers, optical spectrum analyzers, photomultipliers or single photon detectors/counters, and the like. In some cases, detector embodiments may include one or more photodiodes. FIG. 9 depicts aspects (e.g. diode responsivity vs wavelength) of exemplary detector photodiode embodiments. Photodiodes are compact and can have very high bandwidths (10's of MHz to GHz's). A photodiode can measure the amount of light incident on its active surface. A photodiode can be used for measuring attenuation as a function of wavelength in the transmission direction and scatter as a function of wavelength in the backwards direction. In embodiments that involve spanning the whole spectrum from UV to far NIR, more than one type of photodiode may be used.

Figure 10:
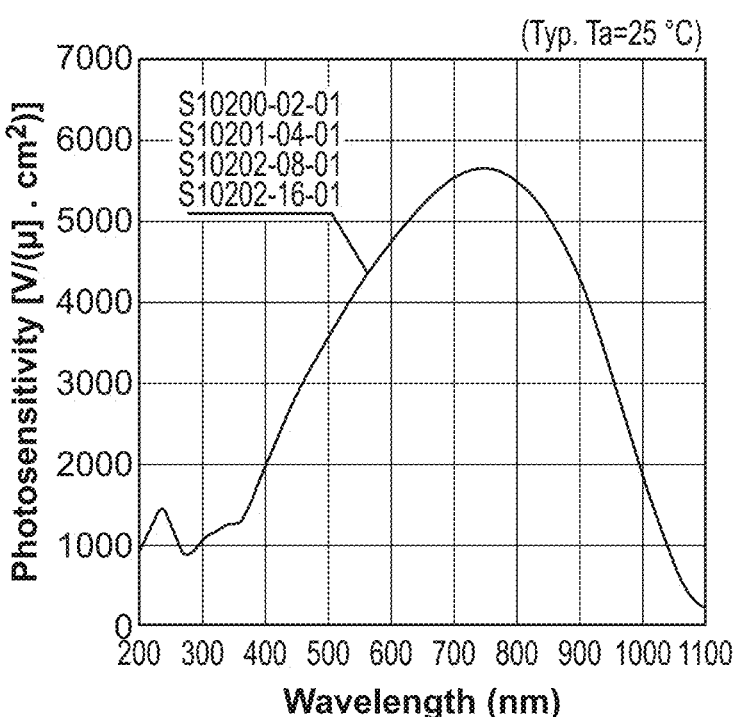
FIG. 10 depicts aspects of a multispectral diagnostic system detector, according to embodiments of the present invention.
Figure 10:
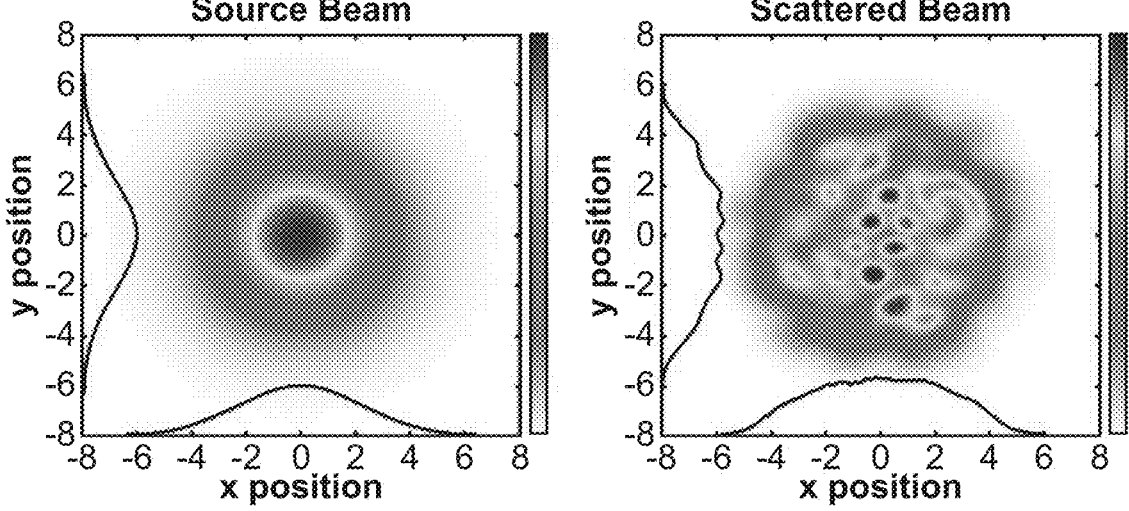

Detector embodiments may include one or more CCD arrays. FIG. 10 depicts aspects of exemplary detector CCD array embodiments. In some cases, a CCD array can be used as an alternative to photodiodes. In some cases, embodiments of the present invention can include a CCD array having a very broad spectral response (e.g. 200 nm-1100 nm) and a high bandwidth (e.g. 10's of kHz).

In some embodiments, a system can use a 2D CCD array. Advantageously, the function of a photodiode can be duplicated by integrating the illuminated power over the area of the CCD. Further advantageously, the exact scatter profile in the forward (T-CCD) and backward (if a S-CCD is being employed) directions can be obtained. Because scatter coefficients can vary as a function of wavelength as well as tissue and constituent types, the scatter profiles as a function of wavelength and time can contain valuable information about the tissue, the blood, and the constituents of the tissue and blood.

Figure 11:
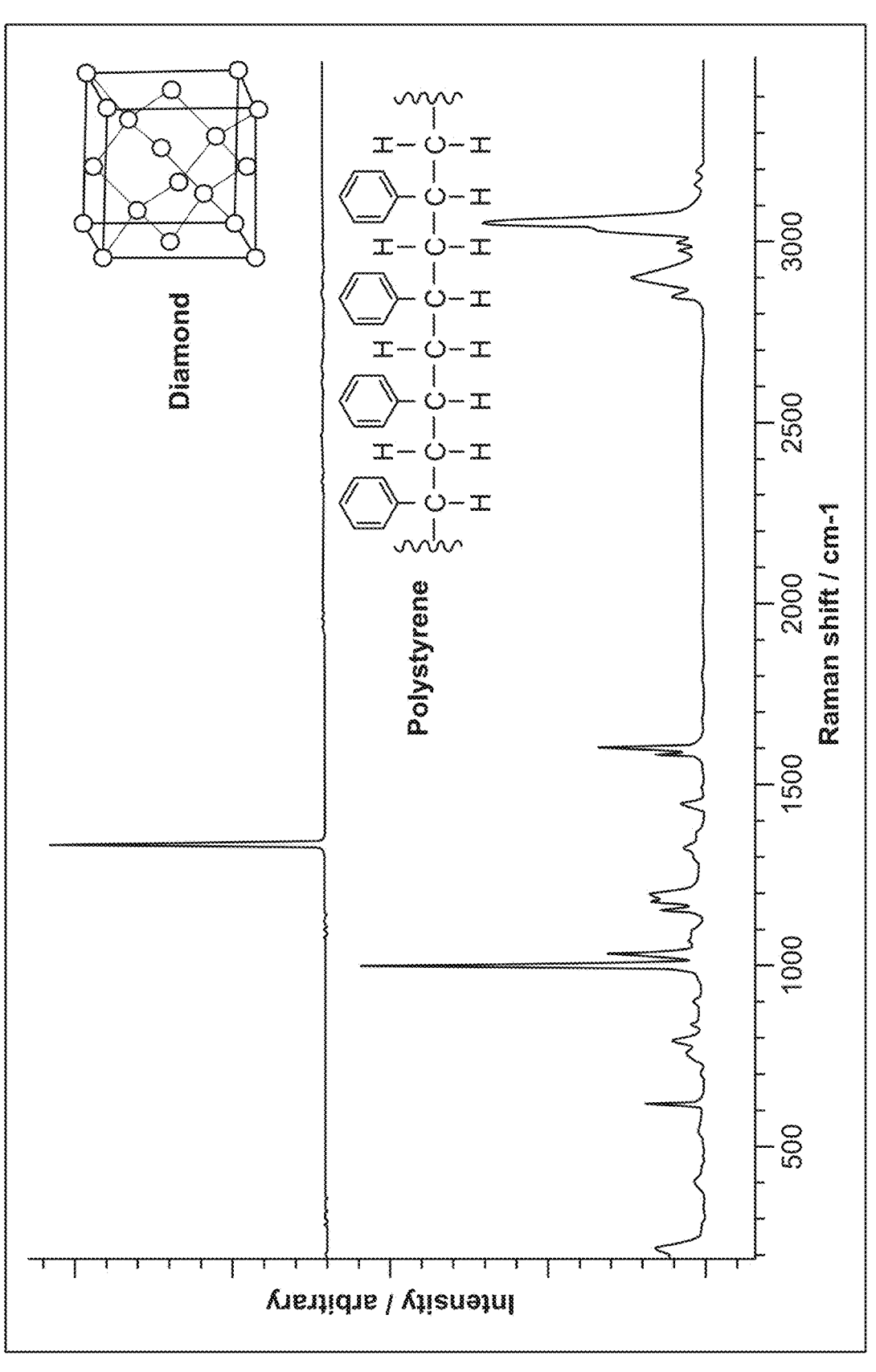
FIG. 11 depicts aspects of a multispectral diagnostic system detector, according to embodiments of the present invention.

Detector embodiments may include a spectrometer or optical spectrum analyzer (OSA). FIG. 11 depicts aspects of exemplary detector spectrometer or OSA embodiments. Spectrometers and OSA's measure the wavelength of light falling on the detector. In some embodiments, the wavelength from the monochromator is known and very narrow (typically <<1 nm). When a photon of light hits a molecule, it may undergo Raman scattering. Raman scattering is the process by which the photon gives up some of its energy in an inelastic collision with the molecule which excites a vibrational or rotational state of a molecule. Because of the loss of energy by the photon, the wavelength of the photon shifts by an exact amount, which is the amount needed to excite the vibrational or rotational quantum state of the molecule. These known wavelength shifts (also known as Raman Stokes shifts) are the fingerprints capable of identifying chemicals, compounds, molecules, enzymes, amino acids, tissue, and any number of other component parts of the target. Additionally, Raman cross sections are wavelength dependent quantities which means there is an added layer of resolution and identification potential that is added to the diagnostic by scanning monochromatically across a broad spectral range or using multiple individual wavelengths.

As an example, the Raman shifts for diamond and polystyrene are shown in FIG. 11. On top of Raman scattering, in the shorter wavelength regimes (UV, violet, and blue), fluorescence may occur. Fluorescence is the process by which a substance is illuminated by energetic photons and the atoms are excited to a higher state. The atoms then re-emit that light often at a longer, very specific wavelength, typically over a longer time period. Fluorescence can be used in diagnostic embodiments. Exemplary spectrometer/OSA embodiments provide the capability to detect fluorescence. Spectrometers can scan thousands of times per second and can be used for intra-heartbeat diagnostics. Spectrometers may operate in wavelength ranges depending on the detector that is being used (similar to photodiodes since many spectrometers use sensors made of the same or similar materials). Additionally, the resolution that can be achieved is set by the desired wavelength range of the spectrometer, with narrower wavelength windows providing better spectral resolution. Therefore, it may be desirable to incorporate more than one spectrometer, or type of spectrometer, into the system in order to scan the entire spectral range with the desired resolution.

Figure 12:
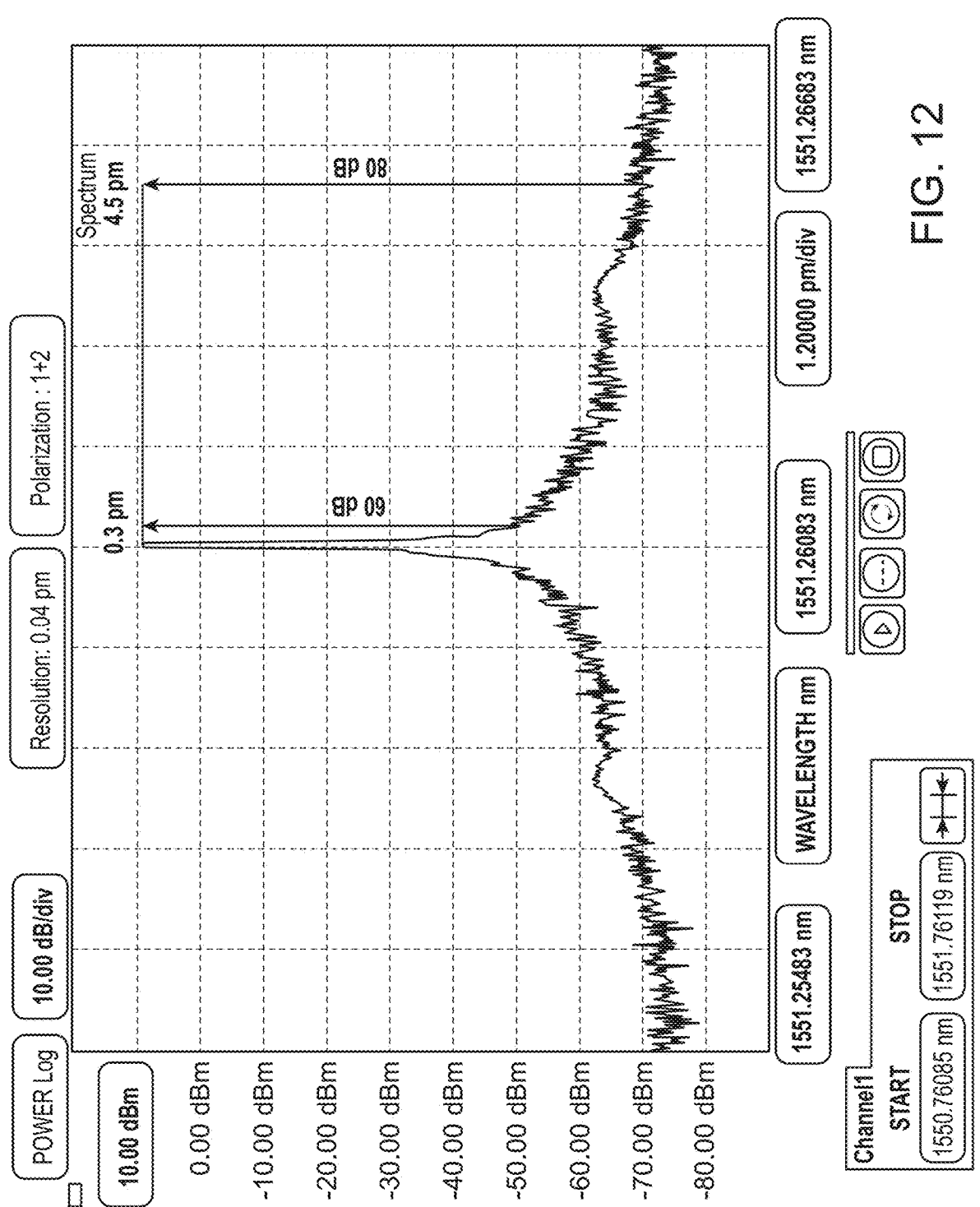
FIG. 12 depicts aspects of a multispectral diagnostic system detector, according to embodiments of the present invention.

FIG. 12 depicts aspects of exemplary detector OSA embodiments. Spectrometers can provide high bandwidths (scans per second) but may be limited in resolution and sensitivity in some instances. If bandwidth is not required, but rather very high resolution (e.g. picometers) and sensitivity (60-80 dB dynamic range), then an optical spectrum analyzer may be used as the detector. Optical spectrum analyzers are capable of scanning the detected output spectrum in great detail but in some cases may suffer the drawback of being slow to scan (10's of nm/sec), and therefore are not currently suitable for doing intra heartbeat pulse diagnostics. However, due to the very high spectral resolution of OSAs, Raman peaks that fall close together or are weak in intensity may be resolved as individual peaks whereas they may overlap with other peaks (i.e. be indistinguishable) or have poor signal to noise ratio with a spectrometer. Relative concentrations of various compounds may be obtained by examining the relative intensity of the peaks observed. This is true for the OSA and spectrometer alike. The function of the photodiodes can be duplicated by integrating the power contained in the spectrum. This is true for the OSA and spectrometer alike.

Figure 13:
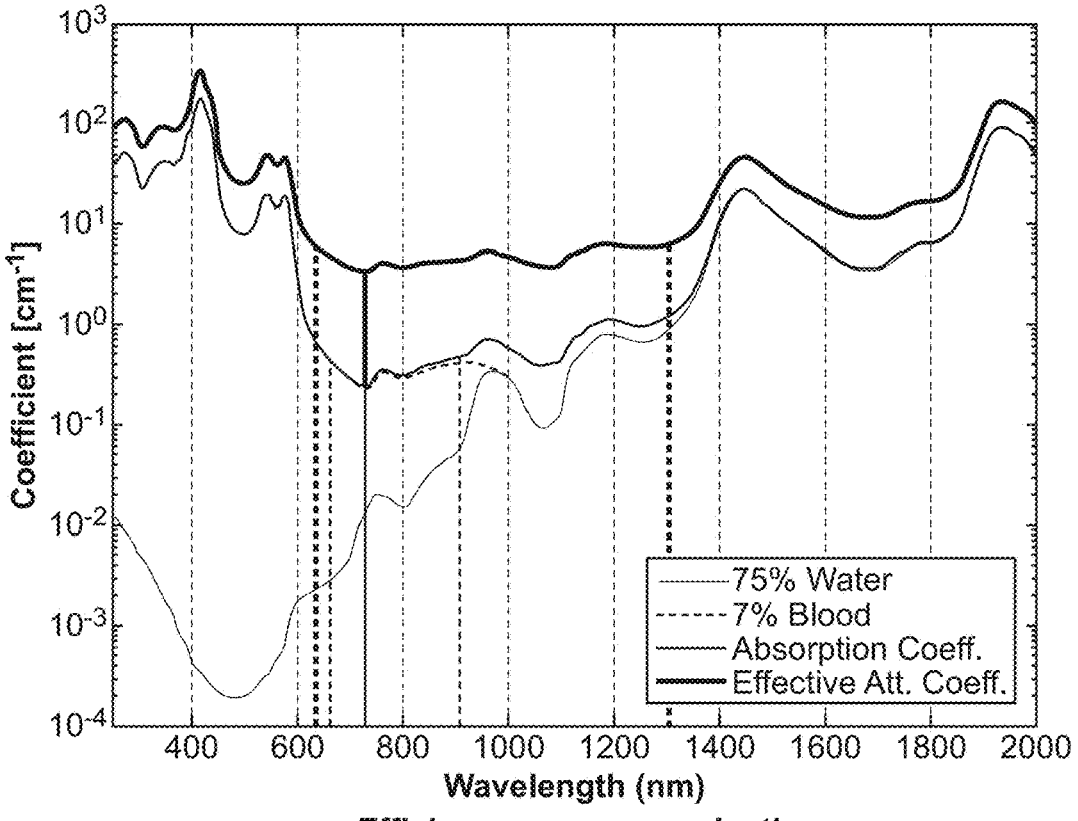
FIG. 13 depicts aspects of a multispectral diagnostic system detector, according to embodiments of the present invention.
Figure 13:
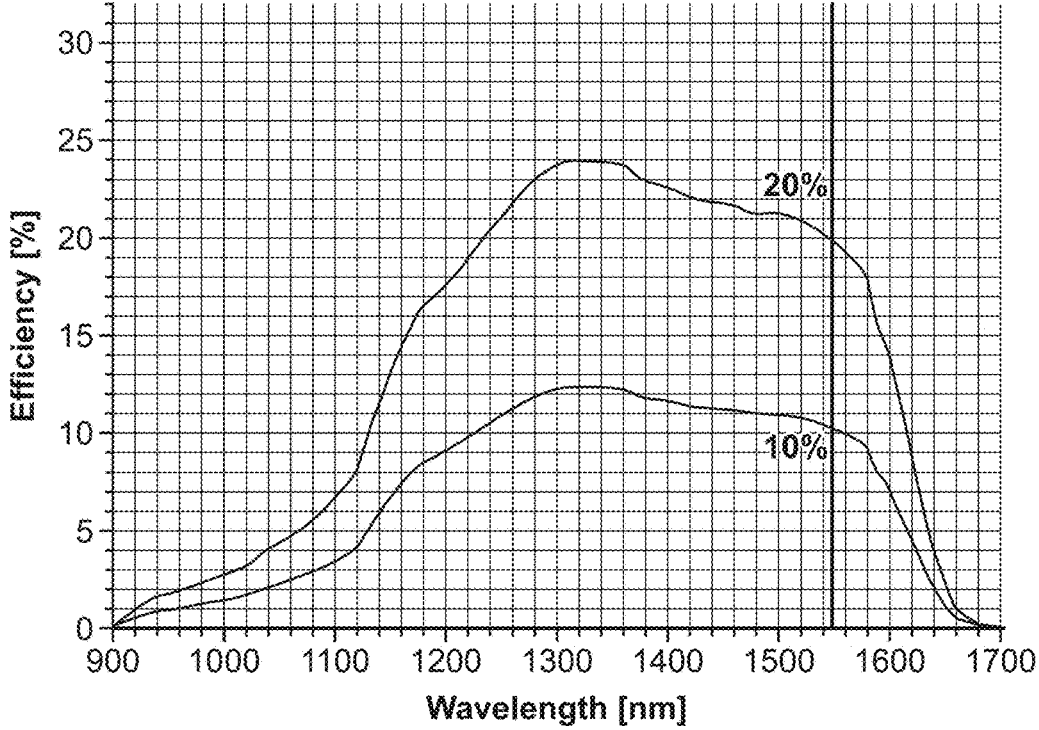

Detector embodiments may include one or more single photon detectors or counters. FIG. 13 depicts aspects of exemplary detector photon detector/counter embodiments. Light is quickly attenuated in human tissue. The absorption spectrum for water and effective attenuation coefficient (scatter and absorption taken into account) for breast tissue is provided here for reference. This means the light is quickly attenuated in very short distances (millimeters or less depending on wavelength). Very sensitive detectors can be used to detect individual photons in the UV, visible, NIR, and SWIR spectra. Despite the high attenuation, some photons may make it to the detector and can be counted, and a spectra can be built. This can allow for comprehensive in vivo diagnostics in relatively unexplored regions of the spectrum (UV, violet, blue, and SWIR for instance). Being able to detect very low signal light levels also allows for diagnostics or imaging of tissue that is deeper in the body as opposed to the limits of thin body parts or near surface diagnostics in use currently.

Figure 14:
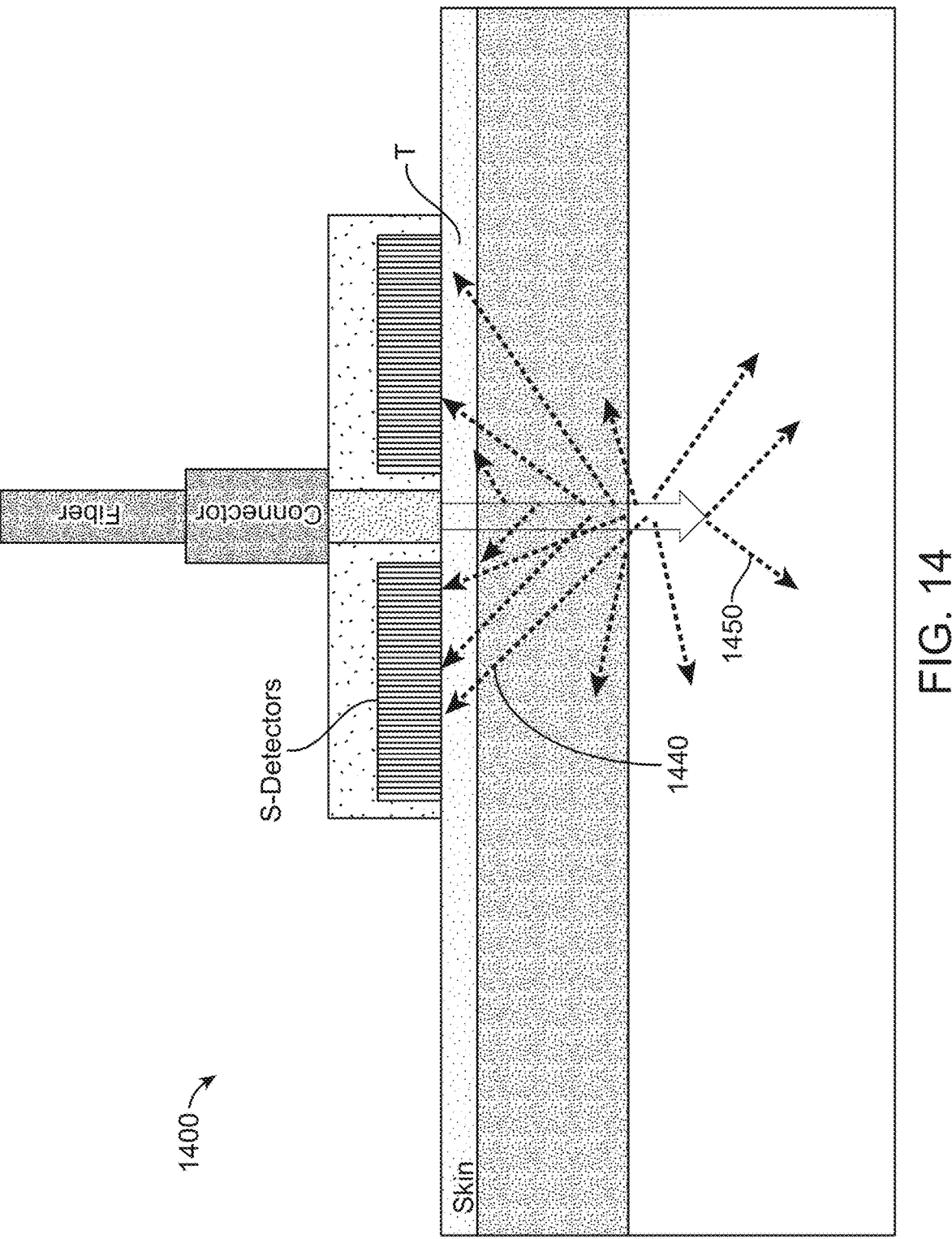
FIG. 14 depicts aspects of a multispectral diagnostic system detector, according to embodiments of the present invention.

FIG. 14 depicts aspects of exemplary backscatter techniques, according to embodiments of the present invention. As discussed elsewhere herein, a device 1400 can be clamped onto a target part T of the body that is thin enough for light transmission to take place (i.e. reach the Transmission detectors), such as a finger, toe, palm, ear lobe, flap of skin, or the like. In some cases, a great deal of diagnostic data can be collected by looking at backscattered light 1440 without the use of transmitted light 1450. This can involve pressing the light source along with backscatter detectors up against the area of interest on the body and taking scanned spectral data in the region of interest. In some cases, this involves obtaining data such as backreflection intensity vs wavelength, scatter profiles, fluorescent emission data, and/or Raman scatter data. The S-Detectors and light source may be integrated into a single device or be separate. Additionally, the use of single photon detectors can allow for deep in vivo photonic diagnostics (e.g. identifying cancerous or other diseased tissue).

In some cases, a detector can include a buried quad junction photodetector (BQJP). A BQJP can be used as a sensor/detector and can play the dual role of spectrometer and photodiode.

Figure 15:
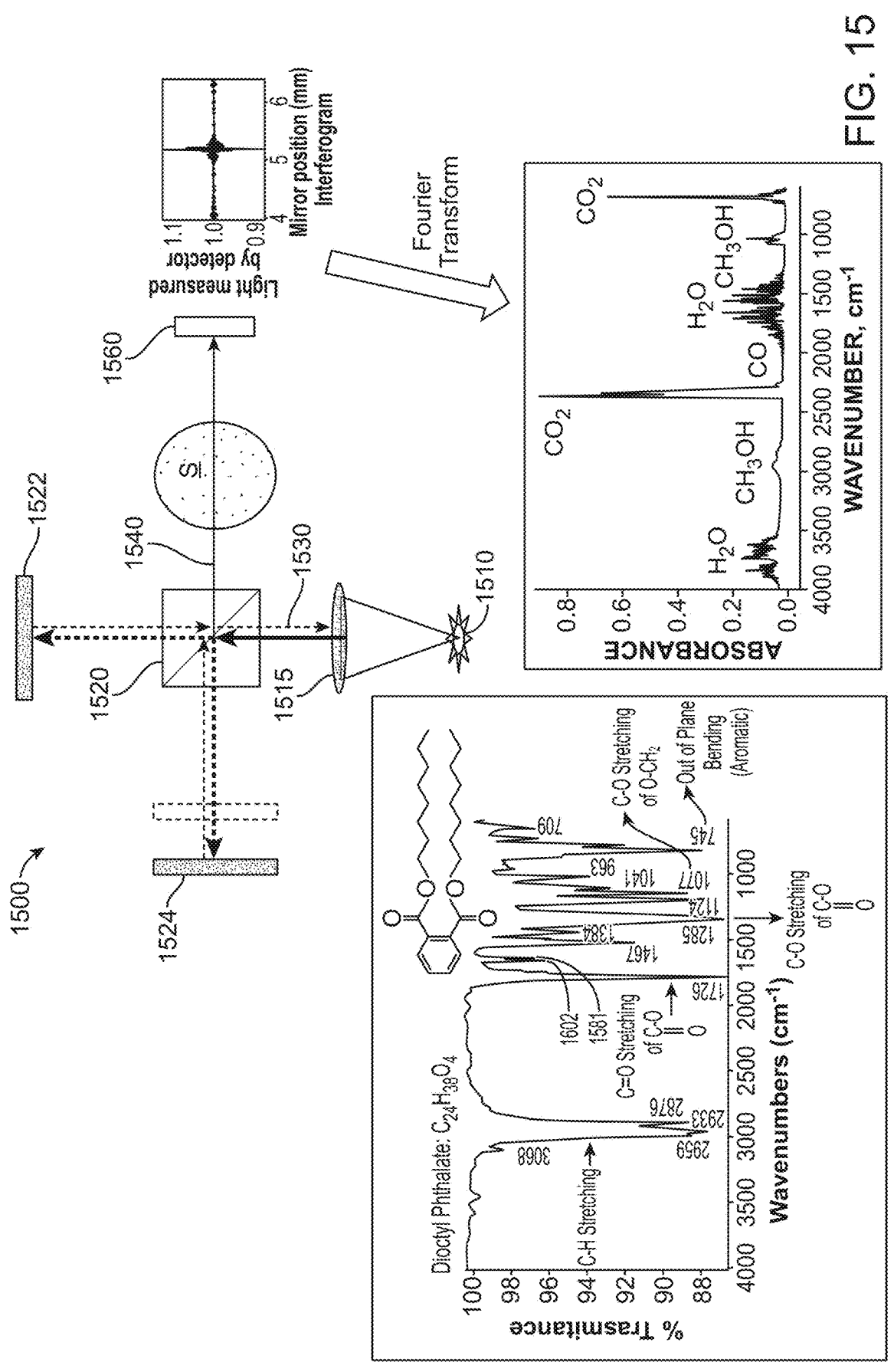
FIG. 15 depicts aspects of a multispectral diagnostic system, according to embodiments of the present invention.

Fourier Transform Infrared Spectroscopy (FTIR) can be used as a spectroscopic technique. FIG. 15 depicts aspects of a layout of an FTIR system 1500. Light provided by a broadband light source or broad spectrum source 1510 can be collimated (e.g. by a collimator 1515) and passed into a 50/50 beam splitter 1520. Half of the beam goes to a fixed mirror 1522 and the other half goes to a movable or translating mirror 1524 (these mirrors can be corner cubes for improved tolerancing). The two reflected beams return to the beam splitter where the beams re-combine. Part 1530 of the re-combined beam is returned to the source and the other part 1540 of the re-combined beam is reflected through the sample S and to a detector 1560 to be inspected.

The re-combined beam intensity oscillates as the various wavelengths experience constructive and destructive interference as their phase is changed by adjusting the optical path length difference, which is done by adjusting the location of the translating mirror. The fluctuations in intensity due to the interferometrics produces an interferogram. When the fixed mirror and the movable mirror are at the same distance all the wavelengths are in phase which produces the maximum intensity for the re-combined beam. This is referred to as the centerburst. As the translating mirror is moved from this point, the intensity will decrease. If a single wavelength is used, the interferogram appears as a sinusoidal trace, involving peaks where the wave constructively interferes with itself and zeros are where the wave destructively interferes with itself.

The Fourier transform of the interferogram through the sample translates the spatial frequency intensities into an absorption spectrum. By comparing to an interferogram with no sample, absorption peaks can be discerned instead of absorption valleys. Both type of spectra, absorption and peaked, are shown here.

FTIR devices can use a He—Ne laser (632.8 nm) to measure the optical path difference between the stationary mirror and the translatable mirror. This is accomplished by counting the number of destructive interferences (nodes) seen in the sinusoidal output of the He—Ne sinewave produced in the interferogram, single/narrow wavelengths produce a sinewave in the interferogram. By the Nyquist sampling theory the position of the movable mirror can be measured to within 632.8 nm. A sine wave of frequency f can be wholly reproduced by sampling at a frequency 2f. There are two interference nodes per translation across the sine wave (doubling the frequency of measured nodes yields 21), therefore, the theoretical limit of detection is 632.8 nm. This method is employed to account for jitter, jerk, and other mechanical instabilities in the system, which will degrade the performance of the spectroscopy.

Figure 16:
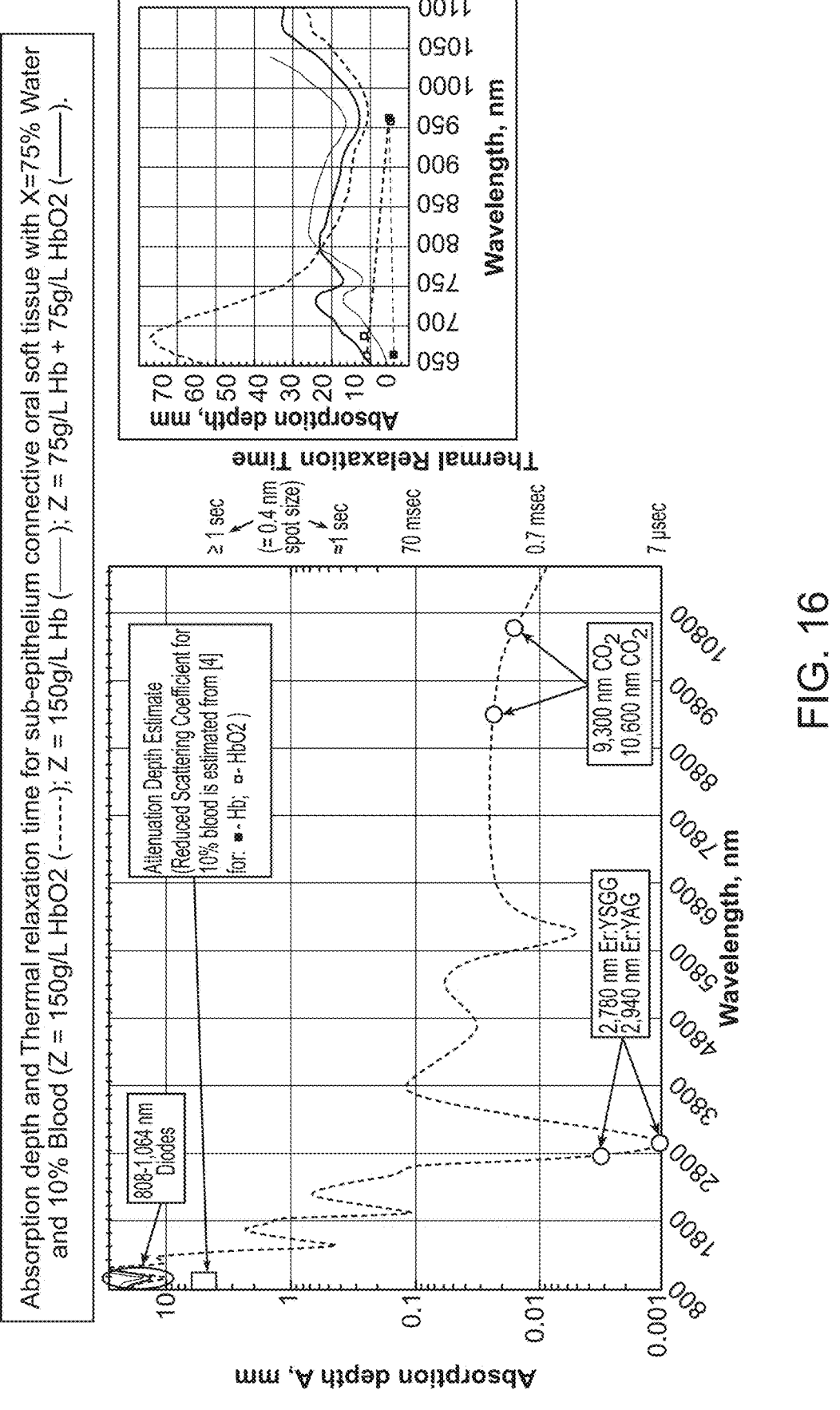
FIG. 16 depicts aspects of a multispectral diagnostic system, according to embodiments of the present invention.

FIG. 16 depicts additional aspects of Fourier Transform Infrared Spectroscopy (FTIR). One advantage of FTIR over dispersive methods, such as grating or prism monochromators, is speed. With FTIR, the entire spectrum can be scanned simultaneously whereas with dispersive methods only a narrow portion of the spectrum can be sequentially scanned at a time. The ability to scan the entire spectrum at once is known as the Felgett Advantage.

FTIR is highly reliable in identifying a wide range of compounds. The technique works on the premise of exciting vibrational and rotational states in molecules, which occur at infra-red energy levels. Infra-red light is very quickly absorbed in tissue and does not penetrate to appreciable depths, as can be seen in the image provided here depicting absorption depth vs wavelength for oral soft tissue. Overtones (harmonics) of the IR molecular excitations will reach into the NIR and visible. However, these overtones will be multiple order harmonics and will be weak in intensity and broad peaked, very difficult to detect and/or distinguish from other peaks if more than one type of material is present.

Conventional FTIR, which identifies molecular content, may not be suitable for certain types of in vivo spectral diagnostics described herein due to the lack of penetration through tissue and the difficulty in detecting higher order harmonics. In some cases, Fourier transform spectroscopy can be implemented at shorter wavelengths.

UV-NIR Fourier Transform Spectroscopy can be used as a spectroscopic technique. FIG. 16 depicts aspects of a UV-Vis-NIR Fourier transform spectrometer. The actuator that manages the optical path difference in a FTIR spectrometer, via the moveable mirror, is typically a stepper motor or other similar mechanical device. The mechanical actuator can be replaced with a linear piezo actuator. Using a piezo actuator as opposed to traditional mechanical actuators has a number of advantages. Piezo actuators are frictionless, are highly controllable, provide fast response times, have stiff mechanical properties, and have sub-nanometer resolution. These properties make piezo actuators excellent, low-noise actuators suitable for short wavelength (UV to NIR) Fourier transform spectroscopy.

Figure 17:
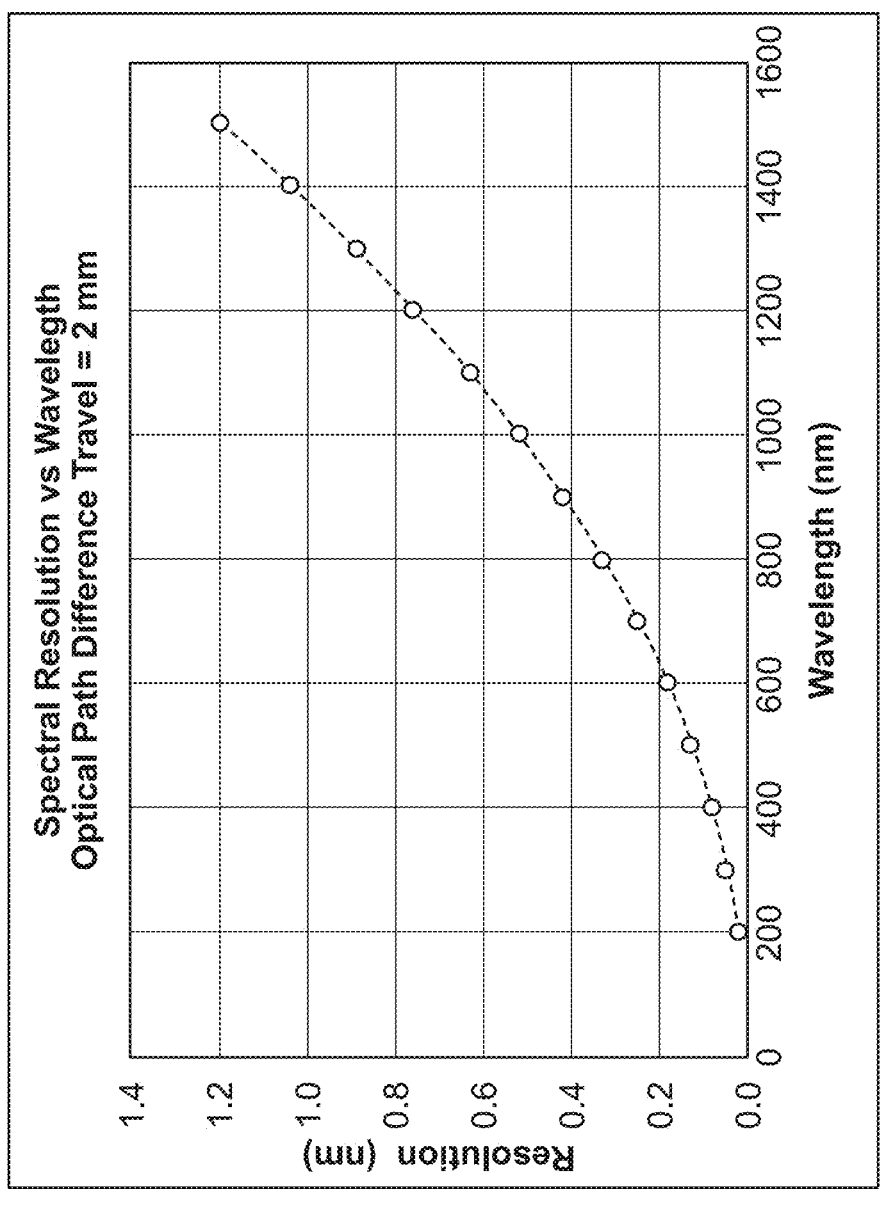
FIG. 17 depicts aspects of a multispectral diagnostic system, according to embodiments of the present invention.

A potential drawback to piezo actuation may be related to a limited travel range, up to 1 mm currently, which equates to a 2 mm optical path difference (in vacuum or air). The spectral resolution achievable by Fourier transform spectroscopy is inversely proportional to the travel range of the movable mirror as well as the wavelength of interest. Mechanical actuators are capable of large travel ranges (>1 cm) and thus very fine spectral resolution. The chart provided in FIG. 17 shows the spectral resolution achievable for wavelengths from 200-1500 nm using a piezo electric actuator with a 2 mm travel range. The spectral resolution that can be achieved is suitable for attenuation and scatter profile methods described herein.

Additionally, laser interferometry can be used to measure the optical path difference between the stationary mirror and the translating mirror, as described with the He—Ne laser elsewhere herein. A shorter wavelength laser can be used to improve the optical path length difference measurement. A frequency tripled Nd:YAG laser is an exemplary embodiment with a wavelength of 355 nm, though other lasers are possible. A frequency tripled Nd:YAG laser can allow Fourier Transform spectroscopy to be achieved down to a wavelength of 355 nm. An Ar2* excimer laser may also be employed which emits at a wavelength of 126 nm. In some cases, the laser is not strictly required. It can be a convenient compensator for imperfections in the mechanical and optical properties of the system.

FTIR can be used to identify materials and molecules through the peaks and/or valleys of the absorption spectra of the irradiated molecules. Infrared is readily absorbed by tissue and the overtones of the molecular vibrational and rotational states may be difficult to detect in the visible and NIR regions. This may make the UV-NIR FT spectroscopy described unsuitable in some cases for the identification of tissue and its constituents via molecular excitation Raman spectroscopy does not suffer from these drawbacks due to the fact that wavelengths that transmit more readily through tissue can be used, and the molecular excitations do not show up as infrared absorption spectra but rather as shifts in the incident wavelength. For these reasons, Raman spectroscopy can be a preferred method for molecular identification when using molecular excitations as the identifying mechanism.

Atomic absorption and fluorescence can be used in the wavelength range described for UV-NIR FT, for example in the UV and visible. Additionally, the tissue can experience bulk attenuation which is a function of the wavelength. The UV-NIR FT technique can detect and map these bulk attenuations that can be used to identify tissue and its constituents as described elsewhere herein.

One advantage of Fourier transform spectroscopy is its speed. The fast scan monochromator described herein has a scan speed suitable for uses described herein, however the UV-NIR FT may provide a more intense light source overall.

Figure 18:
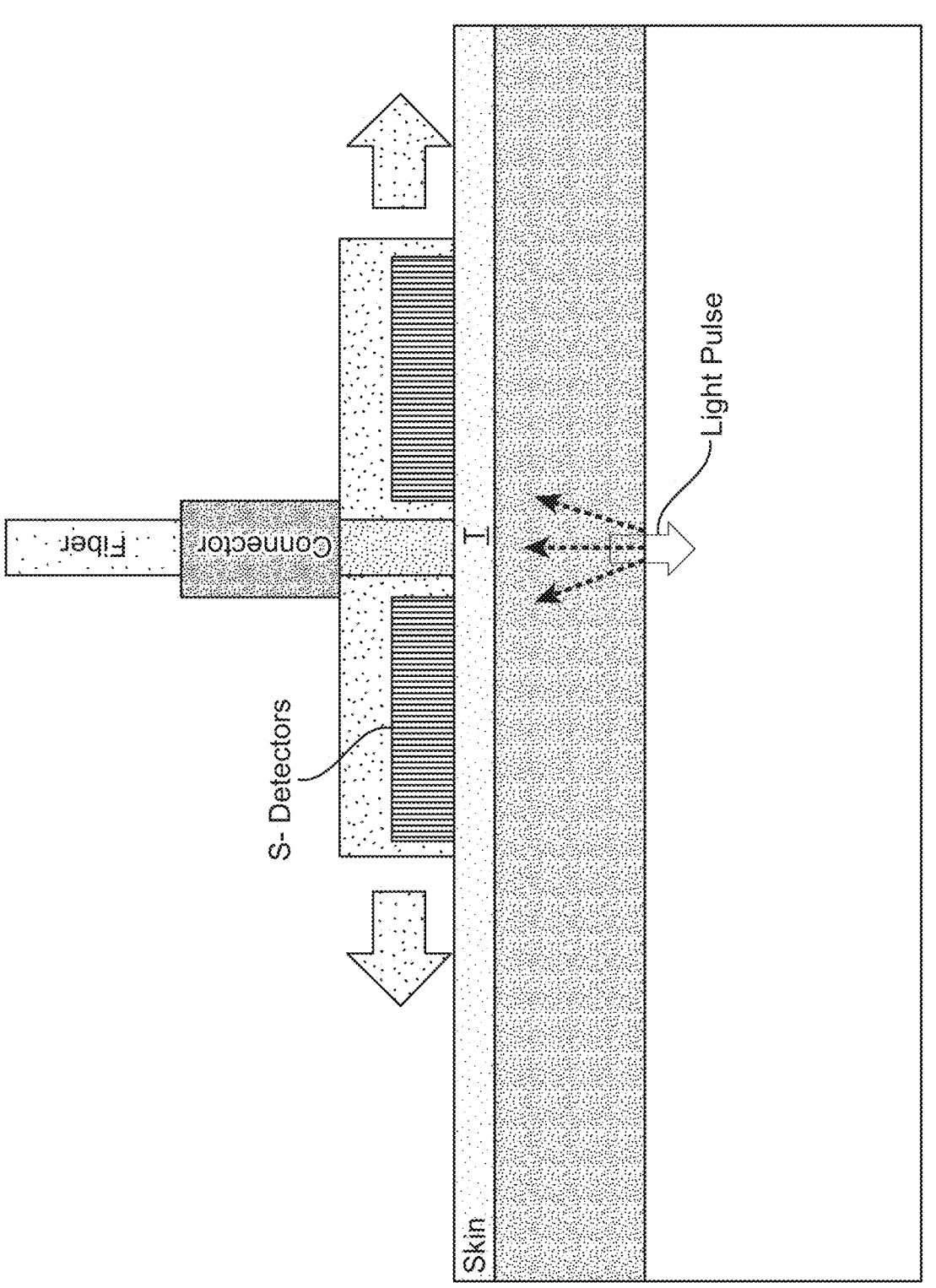
FIG. 18 depicts aspects of a multispectral diagnostic system detector, according to embodiments of the present invention.

FIG. 18 depicts aspects of exemplary Time of Flight Imaging techniques, according to embodiments of the present invention. LIDAR and similar techniques can be used to perform internal body imaging and diagnostics for medicine. In air, light travels at about one foot per second. In a medium, light travels 1/n times the speed of light where n is the index of refraction of the medium. Thus, it is possible to measure distances accurately by the return time of a light pulse. Embodiments of the present invention encompass techniques where a short pulse is sent into the body at the target area T. As the pulse traverses the tissue it can be scattered naturally by the tissue according to the tissue type. Different tissues have different scattering coefficients and different indices of refraction. Additionally, when the pulse traverses an index boundary, from one type of tissue to another, Fresnel reflections can occur at the boundary which can result in a spike in backward reflected light. Over multiple pulses, the attenuation coefficients, scatter coefficients, and index of refractions can be determined as a function of depth.

In some cases, it is possible to do this at a single wavelength. The attenuation coefficients, scatter coefficients, and indices of refraction are all functions of wavelength, therefore in some cases, broad spectral scans as outlined elsewhere herein, or multiply selected wavelengths (e.g. via LEDs or lasers) can provide valuable data on the tissue type and depth.

The source and sensor can be traversed over the target area to create a three-dimensional image. Alternatively, scanning mirrors, beam splitters, and digital light processors (DLPs) can be used to scan the pulsed beam over the volume of interest.

If photomultipliers or single photon detectors are used for the S-Detectors, the imaging depths can be greatly enhanced. The longer the dwell over an area, the deeper the image and the better the clarity that can be created as more scattered photons reach the detector.

Single photon detectors with 15 picosecond temporal resolution and 80 MHz response rate can be used. Light travels 4.5 mm in air in 15 ps. Light travels shorter distances in the same amount of time in a medium due to higher indices of refraction, such as those found in tissue. This means the spatial resolution can be improved in tissue as compared to air. For instance, the 4.5 mm previously stated would be roughly 3.4 mm in water. Also, differential, averaging, and other signal processing techniques and algorithms can be used to further increase the spatial resolution derived from the time of flight measurements.

While the detectors shown in FIG. 18 are in close proximity to the target, it is understood that fiber optics can be used to carry the signal remotely to the detectors. In such cases, it can be helpful to account for pulse dispersion in the fiber optics. In some cases, low dispersion fibers can be used.

Figure 19A:
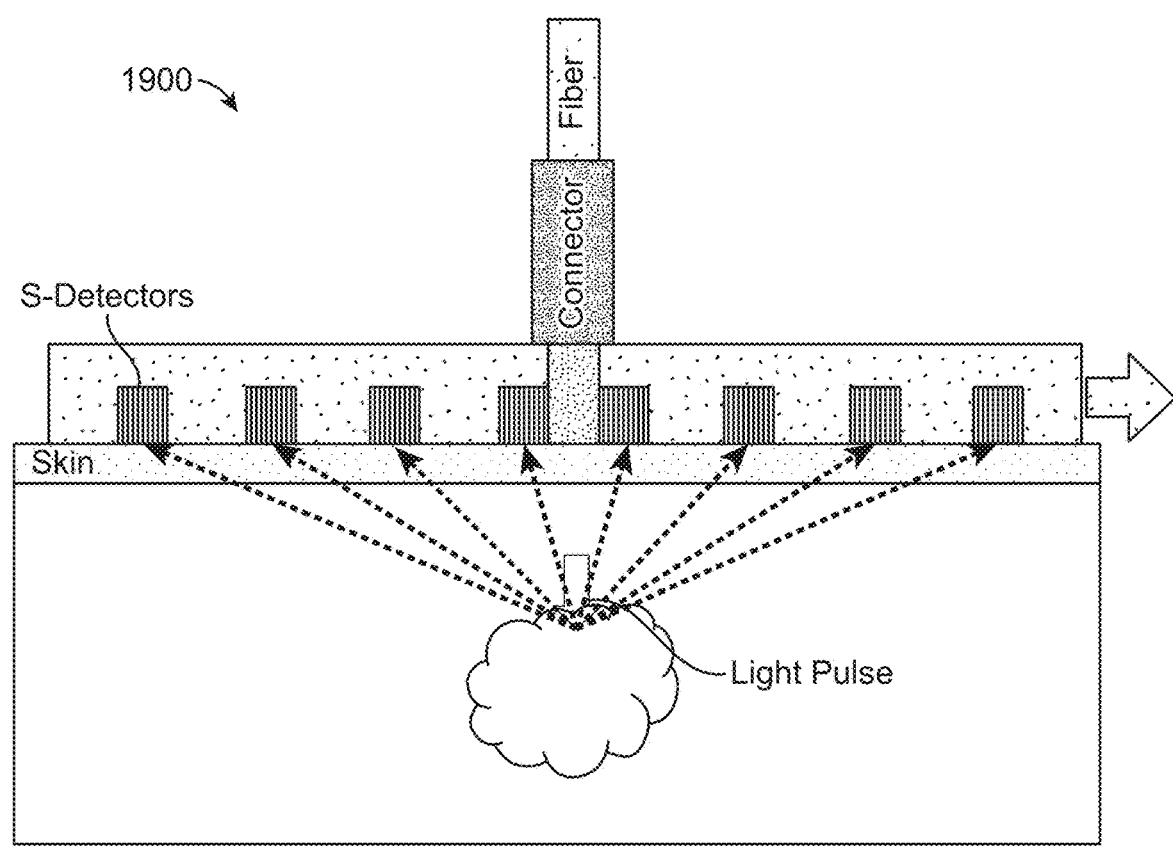
FIGS. 19A and 19B depict aspects of a multispectral diagnostic system detector, according to embodiments of the present invention.
Figure 19B:
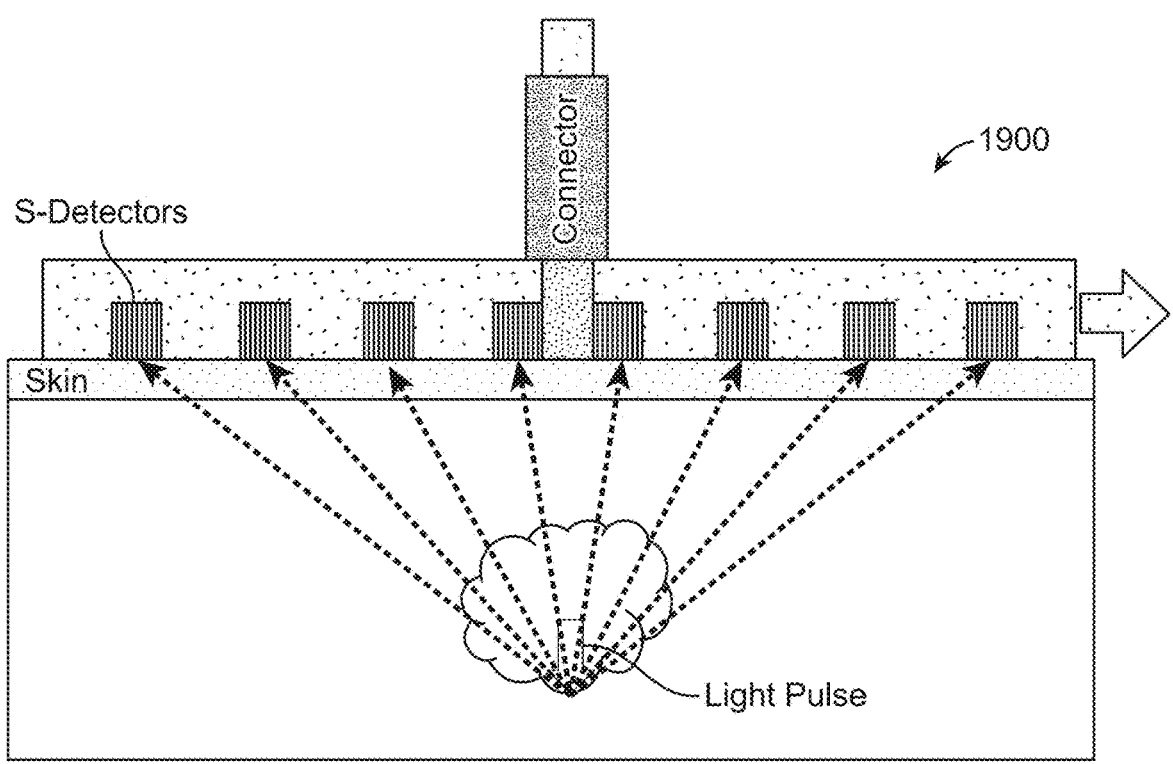

FIGS. 19A and 19B depict aspects of Time of Flight Imaging techniques, according to embodiments of the present invention. One method of improving the accuracy (i.e. clarity and resolution) of the image is to use multiple sensors, for example a matrix of sensors/detectors with multiple sensors.

The time of flight can be different to each sensor; due to the different spacings. This allows for accurate triangulation of scatter points and deconvolution of index of refraction changes as well as absorption and scatter changes throughout the optical path(s). For example, FIG. 19A depicts scatter at an upper portion of a tumor and FIG. 19B depicts scatter at a lower portion of a tumor.

While a planar detection device 1900 is shown for simplicity, any shape can be utilized, including spherical hemisphere, paraboloid, hyperboloid, or any other free form shape (e.g. that maximizes the detection of the backscattered light).

Traditional LIDAR reflects off an opaque surface and provides a profile of that opaque surface, and the light pulse does not propagate past the initial surface. Time of flight imaging embodiments proposed herein can experience partial reflections off of translucent surfaces (can be tissue or body fluids) which include materials/tissue of different indices of refraction and density. Thus, multiple pulses can be received in the detectors as the source pulse makes its way through the tissue and hits interfaces between tissue types or other index of refraction variations, resulting in partial reflections. In addition, a continuous back-scatter intensity profile can be received as the pulse propagates through the bulk tissue(s).

When a strong scatter/reflection of the pulse does occur, such as at an index of refraction boundary (i.e. tissue or fluid boundary), the scatter point can be accurately triangulated. Knowing this position accurately, it is possible to estimate how long the return signal should have taken to reach each of the detectors from the time of launch of the original pulse. The difference in the time of the return pulses and the actual measured returned times indicates the length of time the scatterer molecules and/or atoms are in an excited state before re-emitting their photons. These excitation times can be used to uniquely identify the molecules and/or atoms that are scattering the pulse. This is a special single pulse adaptation of time resolved spectroscopy (TRS). If this is done in the NIR it can be referred to as time resolved NIR spectroscopy (TRNIRS). TRS can be a two pulse process, involving an excitation pulse and a measurement pulse. In some cases, the multiply spaced detectors, which allow for precise location of the scatter point, combined with the picosecond time of flight resolutions, means a single pulse can be used to estimate the excitation and re-emission times of the scatterer. To put it another way, if the location of the scatter point is known, it is possible to calculate how long it should have taken the light pulse to get to that point and back. The time can be longer because at a scatter event the photons are momentarily absorbed by the scatterer material. The amount of time the scatterer holds on to those photons before releasing them is dependent on the material itself, with different atoms/molecules holding on to photons for different times. In this way, atoms/molecules that hold the photon for more time than the temporal resolution of the detector (10's of picoseconds in this example) can be differentiated and classified. In some cases, no staining or labeling is required to identify the species in question.

According to some embodiments, time resolved spectroscopy can be combined with the use of multi-element single photon detectors. The multi-detectors can allow for pinpointing of the point of scatter, allowing for a single pulse and enhanced temporal determination and imaging.

According to some embodiments, Time Resolved NIR Spectroscopy techniques can be used with multiple single photon detectors next to the source, as another way to identify materials, and in conjunction with time of flight imaging.

Figure 20:
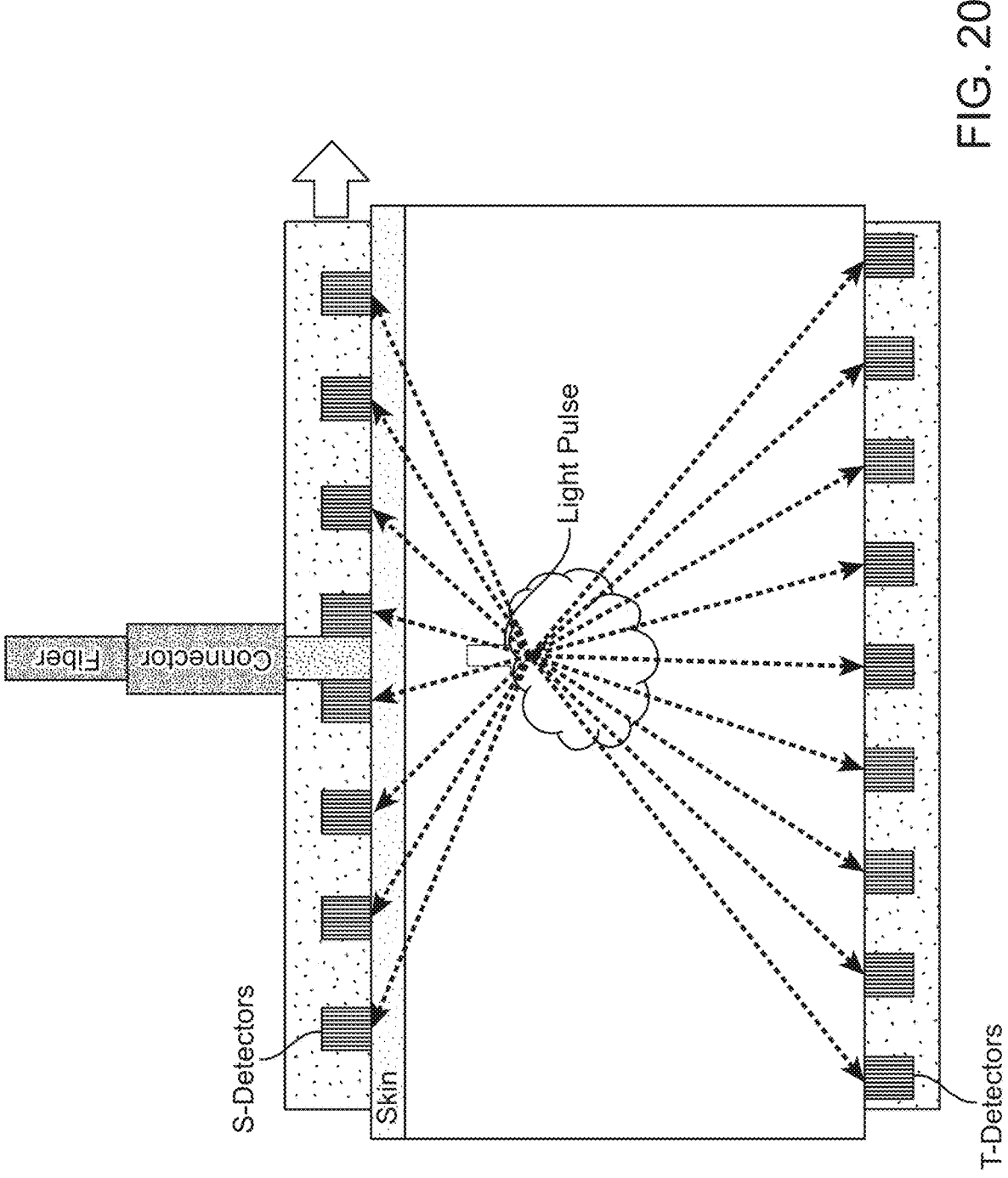
FIG. 20 depicts aspects of a multispectral diagnostic system detector, according to embodiments of the present invention.

FIG. 20 depicts aspects of exemplary Time of Flight Imaging techniques, according to embodiments of the present invention. Aspects of back scattered detection and imaging are discussed elsewhere herein. If wavelength attenuation and tissue thickness allow, transmissive detection and imaging can also be used. When used, transmissive and back-reflected imaging combined can provide an enhanced image.

Figure 21:
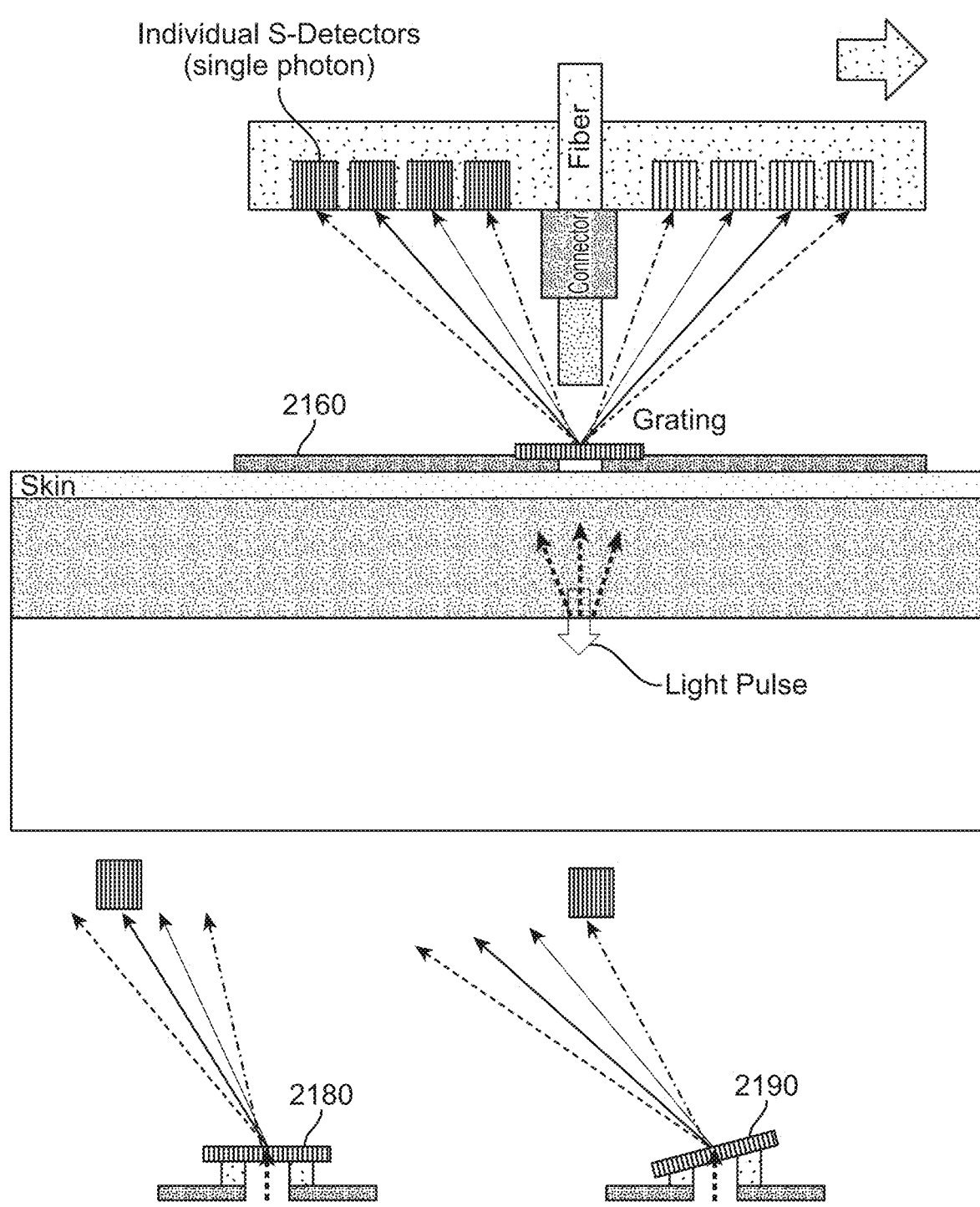
FIG. 21 depicts aspects of a multispectral diagnostic system detector, according to embodiments of the present invention.

FIG. 21 depicts aspects of exemplary Time of Flight Imaging techniques, according to embodiments of the present invention. Time of Flight Imaging techniques can be used in combination with spectral diagnostic techniques. As shown here, a sensor can be configured such that wavelength dependent data, including fluorescence and Raman scattering data, may be collected from the imaged tissue. This allows for accurate classification of the imaged tissue and its constituents, including amino acids, enzymes, lipids, plaques, proteins, drugs, chemicals, cancerous and precancerous cells and the like. No staining or labelling of the species may be required.

The spectral detection involves an aperture or aperture mechanism 2160, which may be referred to as a slit or may otherwise incorporate a slit, to reduce the solid angle of scattered rays entering the dispersion element, in this case a grating though other dispersion elements are possible. A small solid angle may be used to give good spectral resolution and wavelength selectivity, however, there may be a trade off between spectral resolution and time to collect photons at a given wavelength due to the apodization of the incoming beam, thus reducing the total photon flux.

One embodiment involves a stationary grating 2180 with an array of high sensitivity detectors (e.g. single photon detectors or photomultipliers or similar), each detector positioned at a given wavelength dispersion angle from the grating. This method can be efficient at detecting photons returning at a given wavelength. That is, nearly all photons passing through the aperture at a desired wavelength are detected in real time.

Some embodiments involve tilting the grating 2190 on a gimbal, actuators, or any number of other mechanical means such that the backscattered photons are redirected from the grating according to their wavelength and tilt of the grating (via the grating equation shown elsewhere herein). The backscattered photons are scanned (via varying grating tilt) across one or more detectors. This process provides good spectral resolution, however, it may not be as time efficient as other techniques, as it may require a sufficient number of photons to be detected at a given grating tilt (i.e. wavelength) to build a statistically significant spectral profile.

In some cases, the light source can be collimated. The light source can coincide with the grating, and can be launched at an angle to compensate for the dispersion of the grating at the current source wavelength. In other words, the light source can come in at an angle from the side and the grating will turn the light source into the target at a desired incidence angle. The light source can also be close to, but not coincident with, the grating since the scattered solid angle can be of finite size. Scattered light can still enter the grating as long as the light source and grating are in close proximity.

A back scattered spectral configuration is shown here, and a corresponding forward transmission system can be similarly implemented.

Figure 22A:
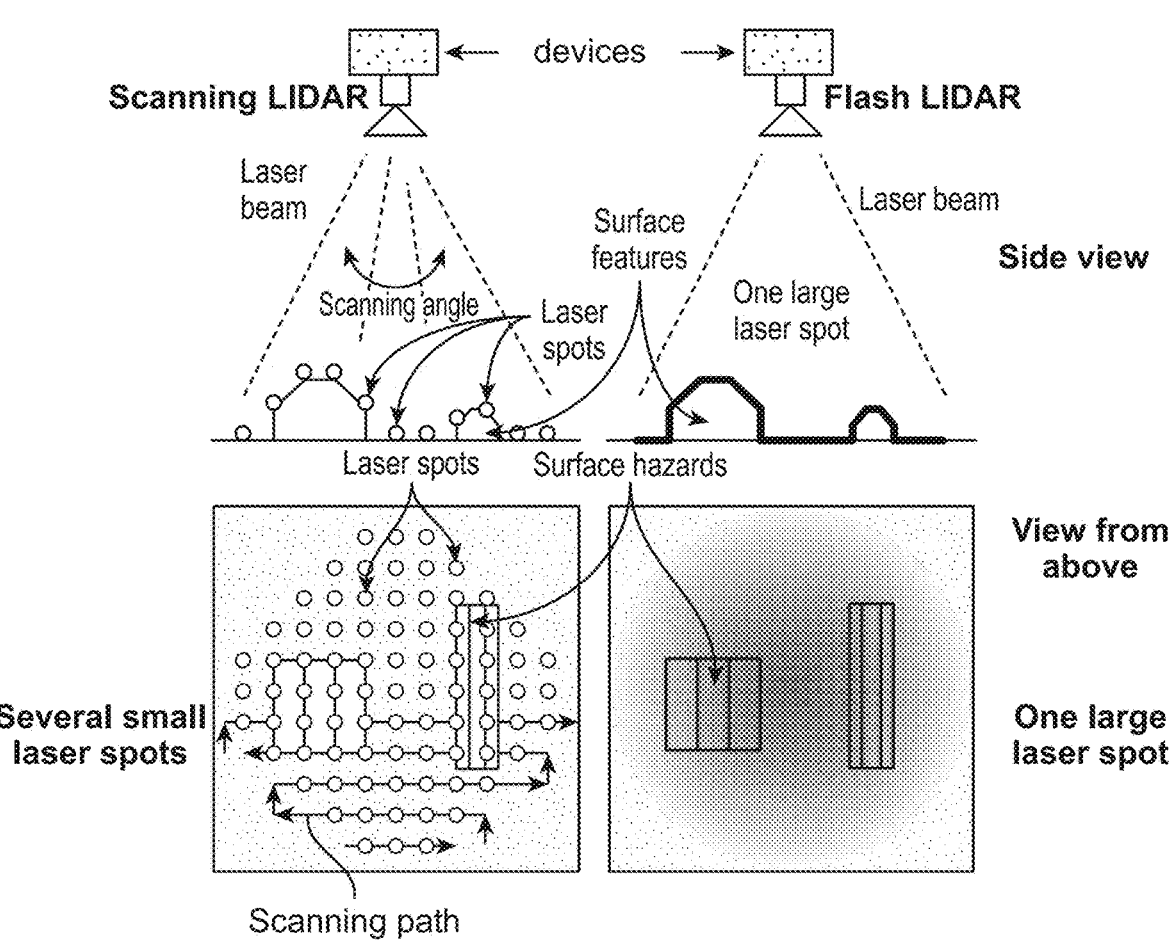
FIGS. 22A and 22B depict aspects of a multispectral diagnostic system, according to embodiments of the present invention.
Figure 22B:
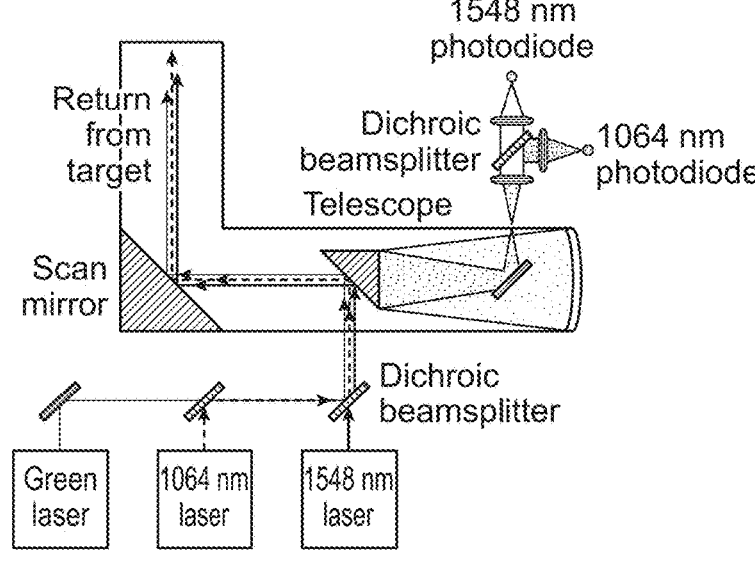

FIG. 22A depicts aspects of Scanning LIDAR vs Flash LIDAR and FIG. 22B depicts aspects of a schematic of a Flash LIDAR beam source. Detectors such as photodiodes, CCDS, photomultipliers, and single photon detectors have been explained alongside single pulse imaging, and Flash LIDAR techniques may be implemented in some instances. Flash LIDAR uses a wide scanning beam with a special matrix detector style camera that converts time of flight (echoes of the beam) into images. Given the appropriate source and detector configurations, Flash LIDAR can be configured for internal body imaging techniques.

Figure 23:
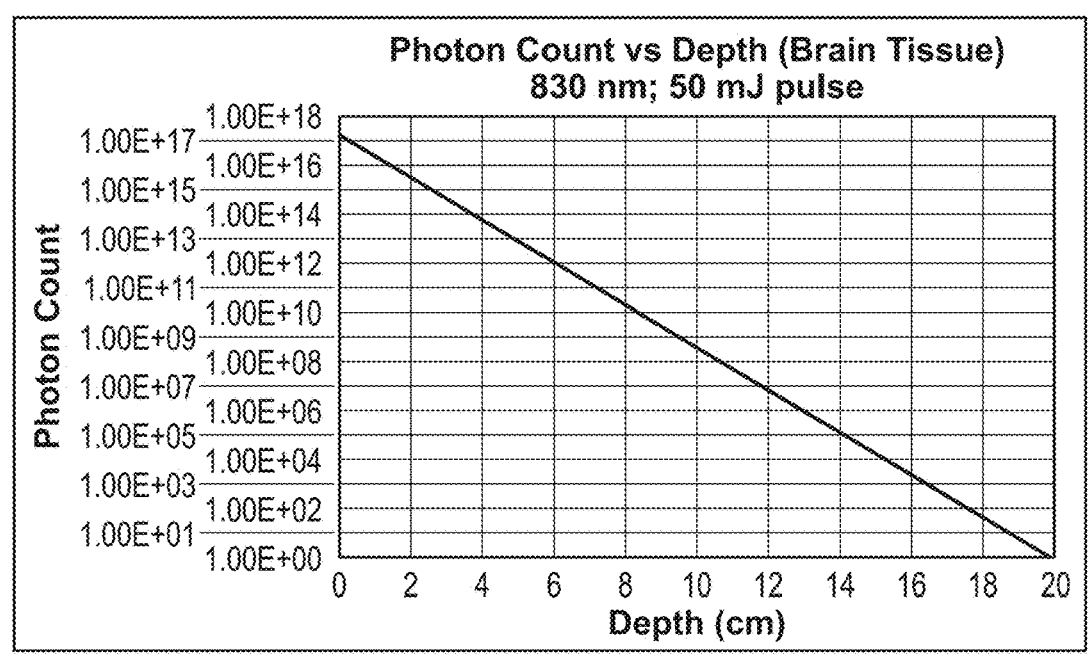
FIG. 23 depicts aspects of a multispectral diagnostic system, according to embodiments of the present invention.
Figure 23:
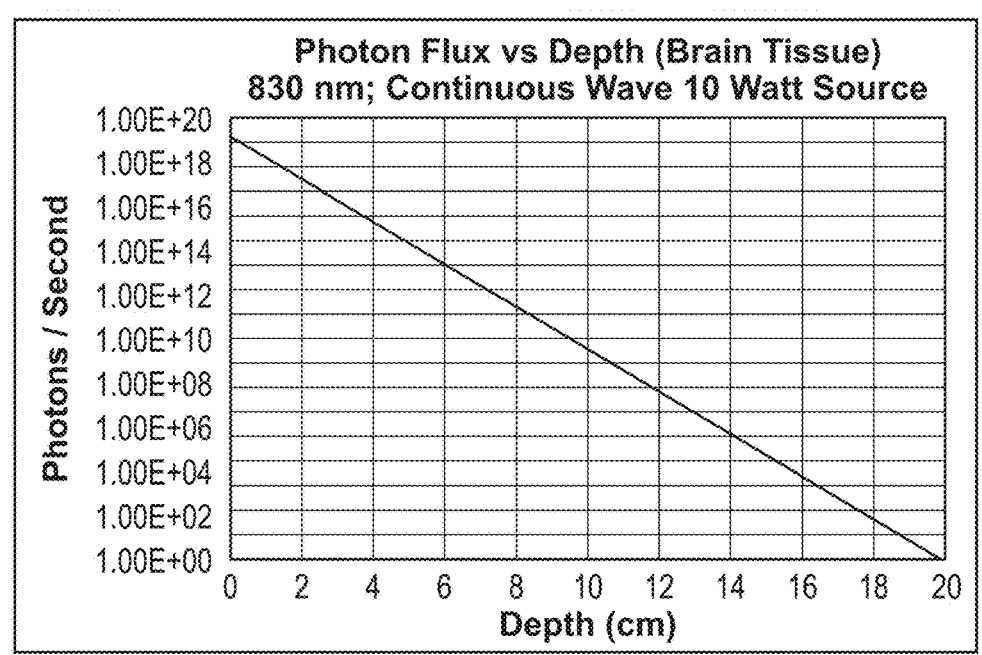

FIG. 23 provides details concerning the depth of penetration, according to some embodiments of the present invention. It has been observed that the effective optical extinction coefficient ($\mu_{eff}$) is 0.14-0.20 mm$^{-1}$ in in vivo brain tissue at 830 nm wavelength. The upper chart, using the Beer-Lambert law, shows the photon count passing through the brain as a function of depth for a 50 mJ pulse at 830 nm wavelength, using the most conservative value stated ($\mu_{eff}$=0.20 mm$^{-1}$).

In a purely transmissive time of flight imaging system, up to 18-20 cm depth may be possible using photomultipliers or single photon detectors. In a back-scattering configuration, depths in the 8-10 cm range are possible. As can be seen from the lower Human Head Berth chart, the entire human head can be imaged when using photomultipliers or single photon detectors to detect low photon fluxes. The human head being just an exemplary example, other body parts/organs are possible.

As an exemplary laser type, a 1053 nm, 10 picosecond pulse, 70 mJ laser can be used for example the EKSPLA PL3143A laser (EKSPLA, Lithuania). A wide variety of lasers with various laser wavelengths and pulse energies can also be used. The energy in the laser pulse, which combined with the wavelength determines the number of photons in the pulse, can help determine the depth of transmission of the detectable pulse.

In non-pulsed applications such as those discussed elsewhere herein, the depth of transmission may be increased by using continuous wave light sources. The middle chart shows the photon flux as a function of depth for a 10 Watt light source at 830 nm. The depth of penetration is beyond 20 cm. Deeper penetrations are possible using higher power light sources, and it may be helpful to consider the duty factor/modulation of the source so as to avoid burning the patient when the power is sufficiently high.

Figure 24:
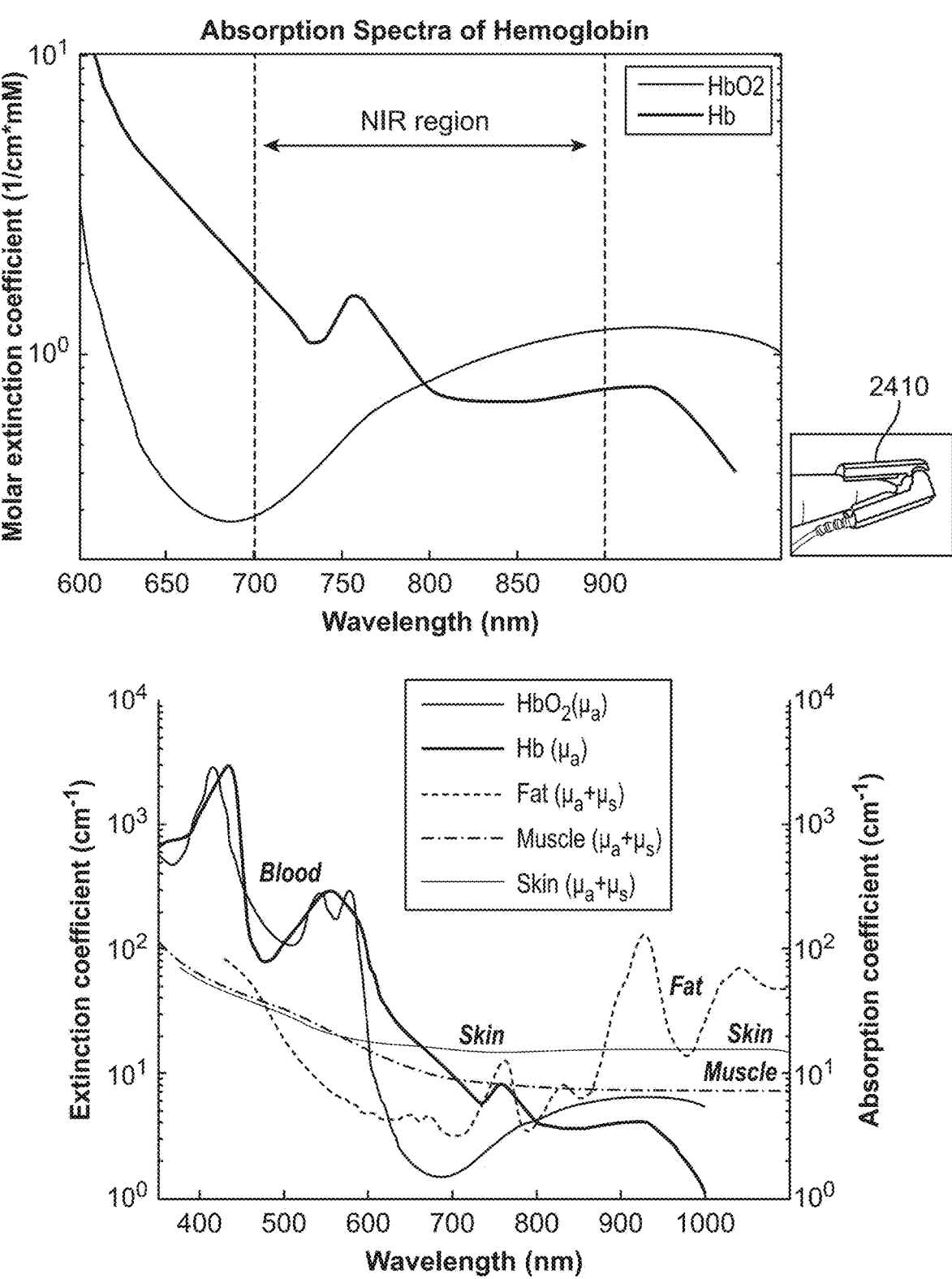
FIG. 24 depicts aspects of a multispectral diagnostic system, according to embodiments of the present invention.

FIG. 24 depicts aspects of pulse oximetry (upper panel) and the optical absorption and extinction coefficients for various tissues (lower panel) that can be used in conjunction with embodiments of the present invention. Pulse oximetry can be performed by passing two wavelengths (e.g. 660 nm and 940 nm) of light through the tip of the finger F and measuring the differential absorption of those two wavelengths using device 2410. Depending on the oxygenation of the blood (i.e. hemoglobin), the absorption coefficient for the two wavelengths differs, thus it is possible to measure the oxygenation of the blood. By adding six additional wavelengths, carboxyhemoglobin (carbon monoxide poisoned hemoglobin) and methemoglobin (hemoglobin that cannot carry oxygen) can also be measured. By analyzing the difference between attenuation at different wavelengths, which may be referred to as differential spectroscopy, it is possible to diagnose some properties of blood. FIG. 24 depicts absorption and extinction coefficients as a function of wavelength for blood and some bulk tissues.

Figure 25:
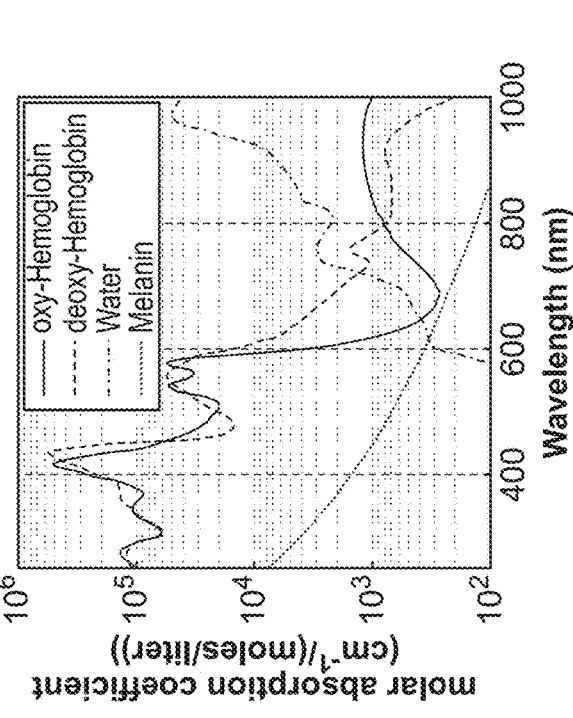
FIG. 25 depicts aspects of a multispectral diagnostic system, according to embodiments of the present invention.
Figure 25:
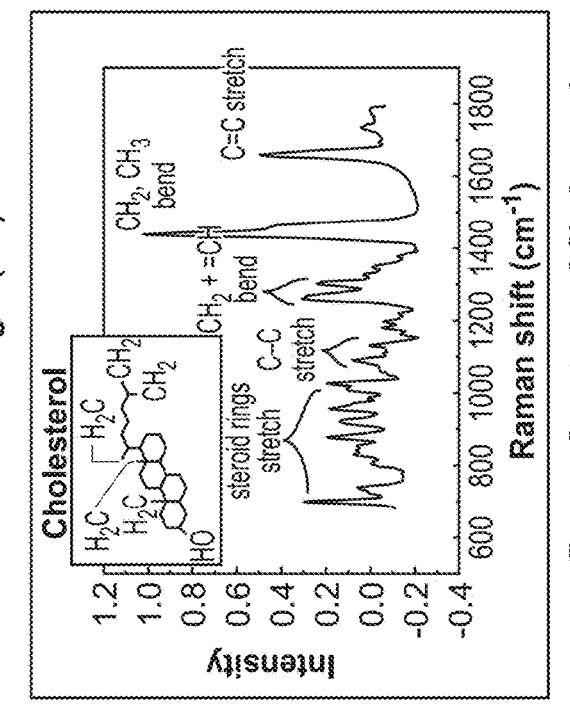
Figure 25:
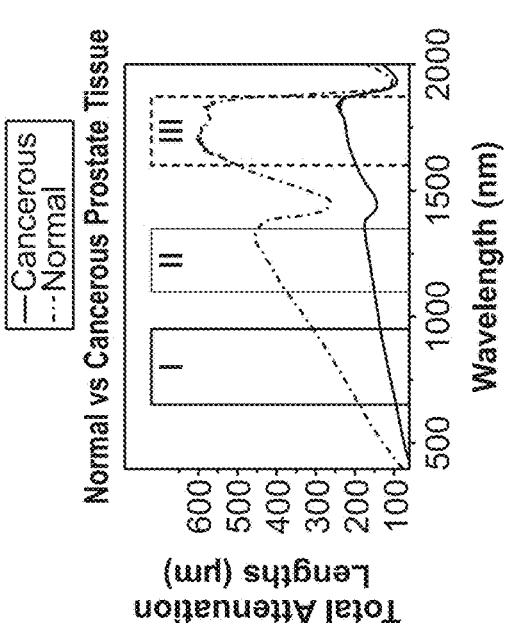
Figure 25:
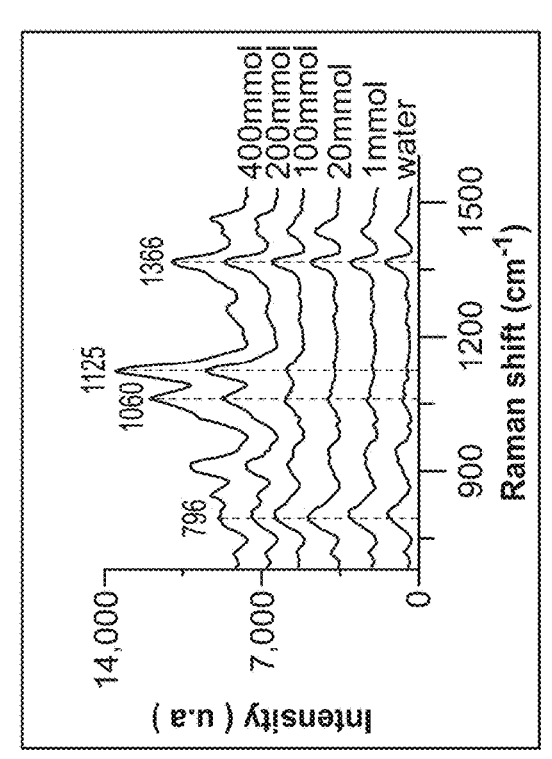

FIG. 25 depicts examples of certain spectra. For example, the broad-spectrum attenuation of healthy prostate tissue vs malignant prostate tissue in vitro is shown. Also depicted is the spectral absorption profile of melanin. The Raman spectrums of glucose as well as cholesterol are also shown. These are examples of spectra that can be measured using the in vivo, non-invasive, diagnostic systems and methods disclosed herein.

Figure 26:
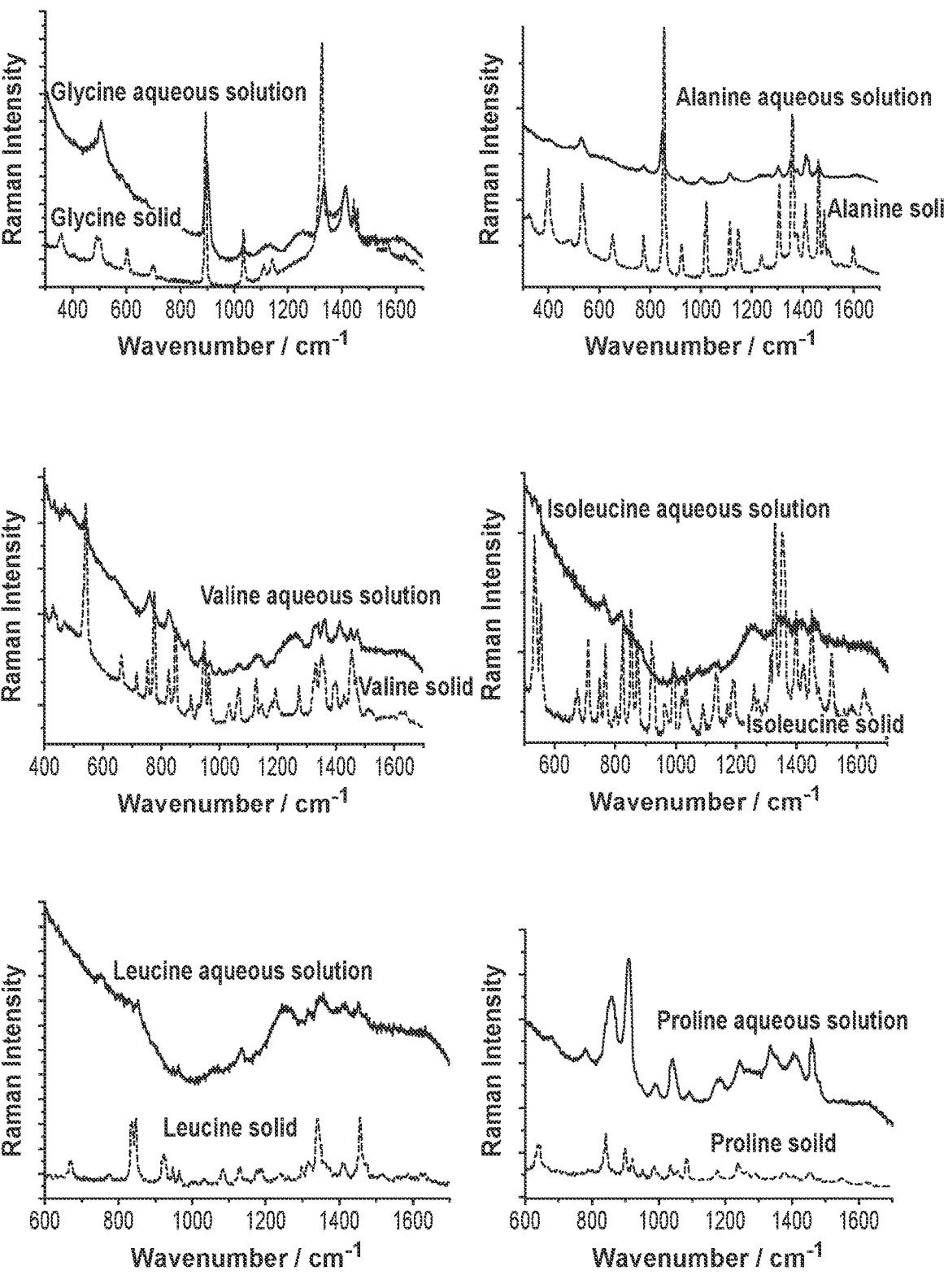
FIG. 26 depicts aspects of a multispectral diagnostic system, according to embodiments of the present invention

FIG. 26 depicts further spectral examples, involving amino acids. These are spectral shifts from the excitation wavelength (Stokes or Raman Scattering shifts as described elsewhere herein), not absolute spectra. Embodiments of the present invention encompass systems and methods for providing significant in vivo spectral data, with the option of multiple spectral and photonic methods, in the realization of non-invasive diagnostics.

In some cases, a multispectral diagnostic system (e.g. which may include a light source, monochromator, delivery mechanism, and/or detector) and/or diagnostic device can further include or be in operative association with a control unit. In some embodiments the control unit may include or be in operative association with a user interface. The control unit can include or be in operative association with one or more processors (e.g. such as processor(s) 1004 depicted in FIG. 27) configured with instructions for performing one or more method steps and operations as described elsewhere herein. Similarly, the control unit may include or be in connectivity with any other component of a computer system (e.g. such as computer system 1000 depicted in FIG. 27).

Figure 27:
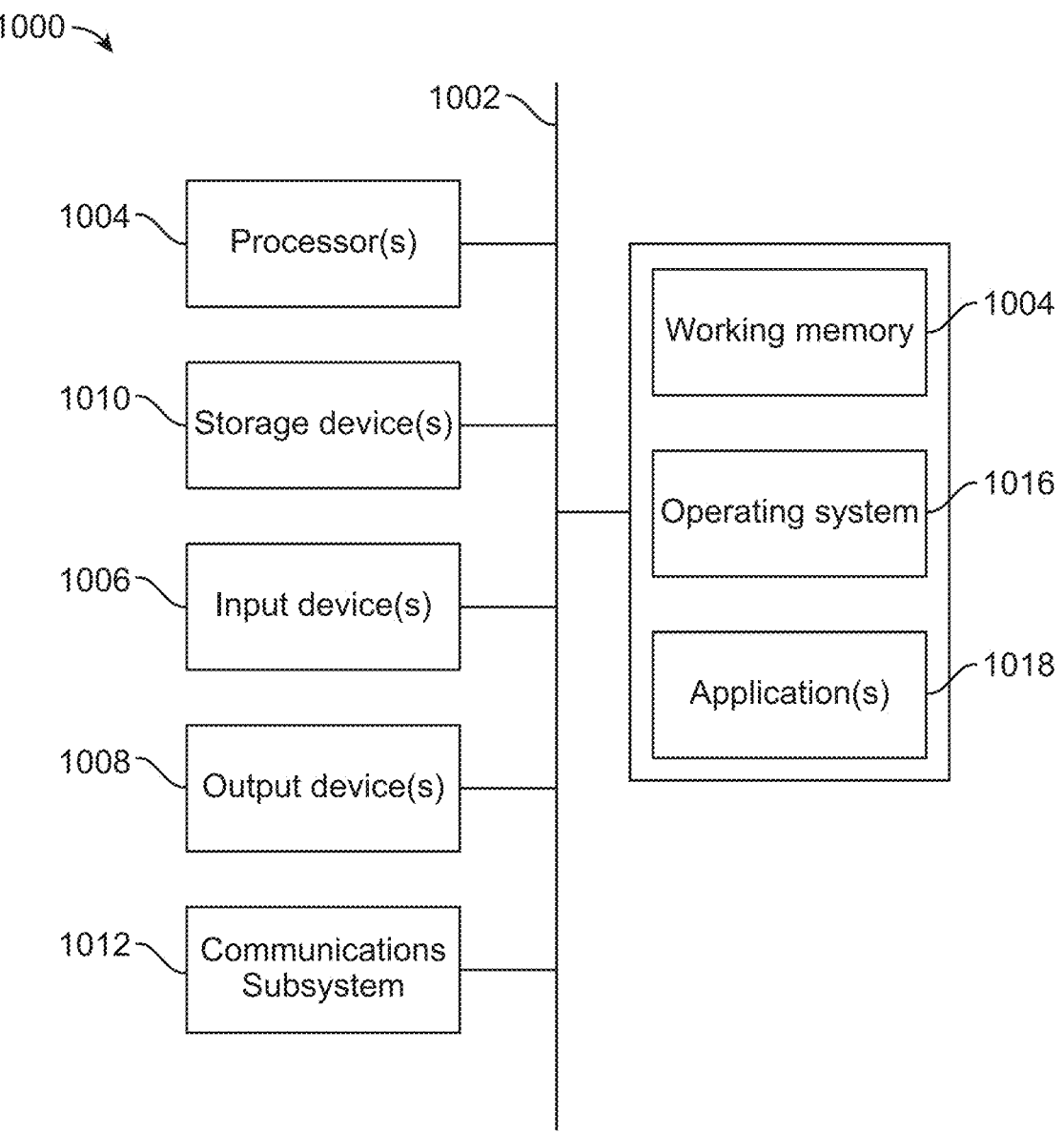
FIG. 27 depicts aspects of a multispectral diagnostic system, according to embodiments of the present invention.

FIG. 27 depicts aspects of an exemplary computer system or device 1000 configured for use with any of the diagnostic systems (or component(s) thereof) or methods disclosed herein, according to embodiments of the present invention. An example of a computer system or device 1000 may include an enterprise server, blade server, desktop computer, laptop computer, tablet computer, personal data assistant, smartphone, any combination thereof, and/or any other type of machine configured for performing calculations. Any computing devices encompassed by embodiments of the present invention may be wholly or at least partially configured to exhibit features similar to the computer system 1000.

The computer system 1000 of FIG. 27 is shown comprising hardware elements that may be electrically coupled via a bus 1002 (or may otherwise be in communication, as appropriate). The hardware elements may include a processing unit with one or more processors 1004, including without limitation one or more general-purpose processors and/or one or more special-purpose processors (such as digital signal processing chips, graphics acceleration processors, and/or the like); one or more input devices 1006, which may include without limitation a remote control, a mouse, a keyboard, a keypad, a touchscreen, and/or the like; and one or more output devices 1008, which may include without limitation a presentation device (e.g., controller screen, display screen), a printer, and/or the like.

The computer system 1000 may further include (and/or be in communication with) one or more non-transitory storage devices 1010, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer system 1000 can also include a communications subsystem 1012, which may include without limitation a modem, a network card (wireless and/or wired), an infrared communication device, a wireless communication device and/or a chipset such as a Bluetooth device, 802.11 device, WiFi device, WiMax device, cellular communication facilities such as GSM (Global System for Mobile Communications), W-CDMA (Wideband Code Division Multiple Access), LTE (Long Term Evolution), and the like. The communications subsystem 1012 may permit data to be exchanged with a network (such as the network described below, to name one example), other computer systems, controllers, and/or any other devices described herein. In many embodiments, the computer system 1000 can further comprise a working memory 1014, which may include a random access memory and/or a read-only memory device, as described above.

The computer system 1000 also can comprise software elements, shown as being currently located within the working memory 1014, including an operating system 1016, device drivers, executable libraries, and/or other code, such as one or more application programs 1018, which may comprise computer programs provided by various embodiments, and/or may be designed to implement methods, and/or configure systems, provided by other embodiments, as described herein. By way of example, one or more procedures described with respect to the method(s) discussed herein, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code can be stored on a non-transitory computer-readable storage medium, such as the storage device(s) 1010 described above. In some cases, the storage medium might be incorporated within a computer system, such as computer system 1000. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, and the like), then takes the form of executable code.

It is apparent that substantial variations may be made in accordance with specific requirements. For example, customized hardware might also be used, and/or particular elements might be implemented in hardware, software (including portable software, such as applets, and the like), or both. Further, connection to other computing devices such as network input/output devices may be employed.

As mentioned elsewhere herein, in one aspect, some embodiments may employ a computer system (such as the computer system 1000) to perform methods in accordance with various embodiments of the disclosure. According to a set of embodiments, some or all of the procedures of such methods are performed by the computer system 1000 in response to processor 1004 executing one or more sequences of one or more instructions (which might be incorporated into the operating system 1016 and/or other code, such as an application program 1018) contained in the working memory 1014. Such instructions may be read into the working memory 1014 from another computer-readable medium, such as one or more of the storage device(s) 1010. Merely by way of example, execution of the sequences of instructions contained in the working memory 1014 may cause the processor(s) 1004 to perform one or more procedures of the methods described herein.

The terms "machine-readable medium" and "computer-readable medium," as used herein, can refer to any non-transitory medium that participates in providing data that causes a machine to operate in a specific fashion. In an embodiment implemented using the computer system 1000, various computer-readable media might be involved in providing instructions/code to processor(s) 1004 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1010. Volatile media may include, without limitation, dynamic memory, such as the working memory 1014.

Exemplary forms of physical and/or tangible computer-readable media may include a floppy disk, a flexible disk, hard disk, magnetic tape, or any other magnetic medium, a compact disc, any other optical medium, ROM, RAM, and the like, any other memory chip or cartridge, or any other medium from which a computer may read instructions and/or code. Various forms of computer-readable media may be involved in carrying one or more sequences of one or more instructions to the processor(s) 1004 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1012 (and/or components thereof) generally can receive signals, and the bus 1002 then can carry the signals (and/or the data, instructions, and the like, carried by the signals) to the working memory 1014, from which the processor(s) 1004 retrieves and executes the instructions. The instructions received by the working memory 1014 may optionally be stored on a non-transitory storage device 1010 either before or after execution by the processor(s) 1004.

It should further be understood that the components of computer system 1000 can be distributed across a network. For example, some processing may be performed in one location using a first processor while other processing may be performed by another processor remote from the first processor. Other components of computer system 1000 may be similarly distributed. As such, computer system 1000 may be interpreted as a distributed computing system that performs processing in multiple locations. In some instances, computer system 1000 may be interpreted as a single computing device, such as a distinct laptop, desktop computer, or the like, depending on the context.

A processor may be a hardware processor such as a central processing unit (CPU), a graphic processing unit (GPU), or a general-purpose processing unit. A processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. All features of the described systems are applicable to the described methods mutatis mutandis, and vice versa. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

According to some embodiments, machine-readable code instructions for, and/or data generated or used by, diagnostic devices, and/or computing devices (which may include smart phones or other mobile computing devices) can be stored on or executed by any of a variety of computing modalities, including without limitation personal computers, servers (e.g. hosted and/or privately owned servers), internet connections, cloud hosts, cloud based storage, and the like.

As described elsewhere herein, a diagnostic device can include or be in operative association with a control unit. In some embodiments the control unit may include or be in operative association with a user interface. The control unit can include or be in operative association with one or more processors configured with instructions for performing one or more method steps (e.g. delivering multispectral light energy to a diagnostic location of a patient). A control unit may include or be in connectivity with any component of a computer system.

All publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A broadband multispectral system for analyzing a tissue of a patient, the system comprising:
    a light source providing an output of light across a broad spectral range;
    a dispersion element, the dispersion element comprising a rotating body having a grating element;
    a first aperture mechanism disposed between the light source and the dispersion element;
    a delivery system;
    a second aperture mechanism disposed between the dispersion element and the delivery system; and
    a detector mechanism,
    wherein the first aperture mechanism allows a portion of the light output by the light source to pass therethrough, wherein the dispersion element spatially separates the portion of the light into components of different wavelengths, wherein the second aperture mechanism allows an amount of the light separated by the dispersion element to pass therethrough, wherein the delivery system transmits the amount of light toward the tissue of the patient to produce resulting light, and wherein the detector mechanism detects the resulting light.

2. The system according to claim 1, wherein the broad spectral range encompasses electromagnetic radiation across a wavelength band from 100 nm to 2000 nm.

3. The system according to claim 1, wherein the light source comprises a member selected from the group consisting of a Xenon arc lamp, a halogen lamp, a carbon arc lamp, a light emitting diode, and a laser diode.

4. The system according to claim 1, wherein the detector mechanism comprises a member selected from the group consisting of a photodiode, a CCD array, a spectrometer, an optical spectrum analyzer, a photomultiplier, a single photon detector, and a single photon counter.

5. The system according to claim 1, wherein the delivery system comprises a member selected from the group consisting of a fiber, a fiber bundle, a liquid light guide, and a gel light guide.

6. The system according to claim 1, wherein the rotating body has a center of mass, and wherein the light source is positioned at the center of mass of the rotating body.

7. A broadband multispectral system for analyzing a tissue of a patient, the system comprising:

a light source providing an output of light across a broad spectral range;

a dispersion element, the dispersion element comprising a rotating body having multiple grating elements, a first aperture mechanism disposed between the light source and the dispersion element;

a delivery system;

a second aperture mechanism disposed between the dispersion element and the delivery system; and a detector mechanism, wherein the first aperture mechanism allows a portion of the light output by the light source to pass therethrough, wherein the dispersion element spatially separates the portion of the light into components of different wavelengths, wherein the second aperture mechanism allows an amount of the light separated by the dispersion element to pass therethrough, wherein the entirety of the broad spectral range is scanned multiple times throughout one rotation of the rotating body, wherein the delivery system transmits the amount of light toward the tissue of the patient to produce resulting light, and wherein the detector mechanism detects the resulting light.

8. The system according to claim 7, wherein the broad spectral range encompasses electromagnetic radiation across a wavelength band from 100 nm to 2000 nm.

9. The system according to claim 7, wherein the light source comprises a member selected from the group consisting of a Xenon arc lamp, a halogen lamp, a carbon arc lamp, a light emitting diode, and a laser diode.

10. The system according to claim 7, wherein the detector mechanism comprises a member selected from the group consisting of a photodiode, a CCD array, a spectrometer, an optical spectrum analyzer, a photomultiplier, a single photon detector, and a single photon counter.

11. The system according to claim 7, wherein the delivery system comprises a member selected from the group consisting of a fiber, a fiber bundle, a liquid light guide, and a gel light guide.

12. The system according to claim 7, wherein the rotating body has a center of mass, and wherein the light source is positioned at the center of mass of the rotating body.

13. A broadband multispectral system for analyzing a tissue of a patient, the system comprising:

a light source providing an output of light across a broad spectral range;

a dispersion element, wherein the dispersion element comprises a cylinder having grating lines etched around a circumference thereof;

a first aperture mechanism disposed between the light source and the dispersion element;

a delivery system;

a second aperture mechanism disposed between the dispersion element and the delivery system; and a detector mechanism, wherein the first aperture mechanism allows a portion of the light output by the light source to pass therethrough, wherein the dispersion element spatially separates the portion of the light into components of different wavelengths, wherein the second aperture mechanism allows an amount of the light separated by the dispersion element to pass therethrough, wherein the delivery system transmits the amount of light toward the tissue of the patient to produce resulting light, and wherein the detector mechanism detects the resulting light.

14. The system according to claim 13, wherein the broad spectral range encompasses electromagnetic radiation across a wavelength band from 100 nm to 2000 nm.

15. The system according to claim 13, wherein the light source comprises a member selected from the group consisting of a Xenon arc lamp, a halogen lamp, a carbon arc lamp, a light emitting diode, and a laser diode.

16. The system according to claim 13, wherein the detector mechanism comprises a member selected from the group consisting of a photodiode, a CCD array, a spectrometer, an optical spectrum analyzer, a photomultiplier, a single photon detector, and a single photon counter.

17. The system according to claim 13, wherein the delivery system comprises a member selected from the group consisting of a fiber, a fiber bundle, a liquid light guide, and a gel light guide.

18. The system according to claim 13, wherein the grating lines are present in a grating pattern that is repeated periodically around the circumference.

19. The system according to claim 13, wherein the cylinder has a center of mass, and wherein the light source is positioned at the center of mass of the rotating body.

* * * * *